(12) United States Patent
Ravid et al.

(10) Patent No.: US 9,631,919 B2
(45) Date of Patent: Apr. 25, 2017

(54) NON-CONTACT SHEET RESISTANCE MEASUREMENT OF BARRIER AND/OR SEED LAYERS PRIOR TO ELECTROPLATING

(71) Applicant: APPLIED MATERIALS, INC., Santa Clara, CA (US)

(72) Inventors: Abraham Ravid, San Jose, CA (US); Dmitry A. Dzilno, Sunnyvale, CA (US); Todd J. Egan, Fremont, CA (US); Robert O. Miller, Bayville, NY (US)

(73) Assignee: Applied Materials, Inc., Santa Clara, CA (US)

( * ) Notice: Subject to any disclaimer, the term of this patent is extended or adjusted under 35 U.S.C. 154(b) by 578 days.

(21) Appl. No.: 14/066,005

(22) Filed: Oct. 29, 2013

(65) Prior Publication Data

US 2014/0367265 A1    Dec. 18, 2014

Related U.S. Application Data

(60) Provisional application No. 61/834,353, filed on Jun. 12, 2013.

(51) Int. Cl.
  *G01R 31/02*  (2006.01)
  *G01B 7/06*  (2006.01)
  (Continued)

(52) U.S. Cl.
  CPC .......... *G01B 7/105* (2013.01); *C25D 17/001* (2013.01); *C25D 21/12* (2013.01); *G01N 27/20* (2013.01); *C25D 7/123* (2013.01); *C25D 17/12* (2013.01)

(58) Field of Classification Search
  CPC ....... H01L 22/14; G01R 3/00; G01R 31/2831; G01R 1/07342; G01R 31/2884;
  (Continued)

(56) References Cited

U.S. PATENT DOCUMENTS 4,000,458 A    12/1976 Miller et al.
4,425,545 A    1/1984 Scalese
(Continued)

FOREIGN PATENT DOCUMENTS

CN    102183198    9/2011
JP    2000-180143 A    6/2000
(Continued)

OTHER PUBLICATIONS

Official Action Dated Jan. 28, 2016 Issued in Co-Pending U.S. Appl. No. 13/998,741.
(Continued)

*Primary Examiner* — Vinh Nguyen
(74) *Attorney, Agent, or Firm* — Fish & Richardson P.C.

(57) ABSTRACT

A measurement tool for measuring an electrical parameter of a metal film deposited on a front side of a workpiece includes an electrical sensor connected to a workpiece contact point, an energy beam source with a beam impact location on the front side, a holder and a translation mechanism capable of translating the holder relative to the workpiece support, the beam source supported on the holder, and a computer programmed to sense a behavior of an electrical parameter sensed by the sensor.

10 Claims, 22 Drawing Sheets

(51) Int. Cl.
*C25D 21/12* (2006.01)
*G01N 27/20* (2006.01)
*C25D 17/00* (2006.01)
*C25D 7/12* (2006.01)
*C25D 17/12* (2006.01)

(58) Field of Classification Search
CPC .............. G01R 1/0735; G01R 31/2886; G01R 1/07314; G01R 1/06711; G01R 31/2863; G01R 1/06744; G01R 1/06727; G01R 1/06761; G01R 1/07357; G01R 31/2853; G01R 31/2891; G01R 33/093; G01R 1/0491; G01R 1/06794; G01R 27/205; G01R 31/129; G01R 31/316; G01R 33/0005; G01R 35/00; G01R 35/005; G01N 21/9501; G01N 2021/8854; G01N 2033/00; G01N 21/68; G01N 21/8422; G01N 2291/0256; G01N 2291/0423; G01N 2291/106; G01N 2291/2697; G01N 27/4146; G01N 29/022; G01N 29/036; G01N 29/14; G01N 29/223; G01N 2033/0095; G01N 21/55; G01N 12/523; H01R 12/523; H01R 13/2414; H01R 2201/20
See application file for complete search history.

(56) References Cited

U.S. PATENT DOCUMENTS

| | | | |
|---|---|---|---|
| 4,752,739 A | 6/1988 | Wang | |
| 5,365,034 A * | 11/1994 | Kawamura | G01R 31/311 219/121.69 |
| 5,493,236 A * | 2/1996 | Ishii | G01R 31/2656 324/501 |
| 6,072,313 A | 6/2000 | Li et al. | |
| 6,563,308 B2 | 5/2003 | Nagano et al. | |
| 6,597,182 B1 * | 7/2003 | Tachibana | C25D 21/12 324/537 |
| 6,691,576 B1 | 2/2004 | Sato et al. | |
| 7,071,713 B2 * | 7/2006 | Furukawa | G01R 31/307 250/492.2 |
| 7,242,185 B1 | 7/2007 | Bailey, III | |
| 7,868,631 B2 * | 1/2011 | Chen | H02S 50/10 324/754.23 |
| 2002/0142493 A1 | 10/2002 | Halliyal et al. | |
| 2003/0067298 A1 | 4/2003 | Nagano et al. | |
| 2003/0206009 A1 | 11/2003 | Le | |
| 2004/0207395 A1 | 10/2004 | Sarfaty et al. | |
| 2005/0083048 A1 | 4/2005 | Lei et al. | |
| 2005/0183959 A1 | 8/2005 | Wilson et al. | |
| 2006/0243598 A1 | 11/2006 | Singh et al. | |
| 2006/0284089 A1 | 12/2006 | Fischer | |
| 2008/0118631 A1 | 5/2008 | Tsai et al. | |
| 2009/0256558 A1 | 10/2009 | Fujita et al. | |
| 2009/0301894 A1 | 12/2009 | Ehlers et al. | |
| 2010/0187094 A1 | 7/2010 | Fukao et al. | |
| 2012/0270477 A1 | 10/2012 | Nangoy et al. | |
| 2013/0133575 A1 | 5/2013 | Gauje | |
| 2014/0002062 A1 | 1/2014 | Lu et al. | |

FOREIGN PATENT DOCUMENTS

| | | |
|---|---|---|
| KR | 10-2010-0044899 | 4/2010 |
| KR | 10-2010-0044899 A | 4/2010 |
| WO | WO-2011151530 A1 | 12/2011 |

OTHER PUBLICATIONS

U.S. Appl. No. 14/066,092, filed Oct. 29, 2013, Egan et al.
U.S. Appl. No. 13/998,741, filed Oct. 29, 2013, Ravid et al.
Clark, Raymond H. "Handbook of Printed Circuit Manufacturing." 1985, p. 290, Van Nostrand Reinhold Co., Inc., New York, U.S.

* cited by examiner

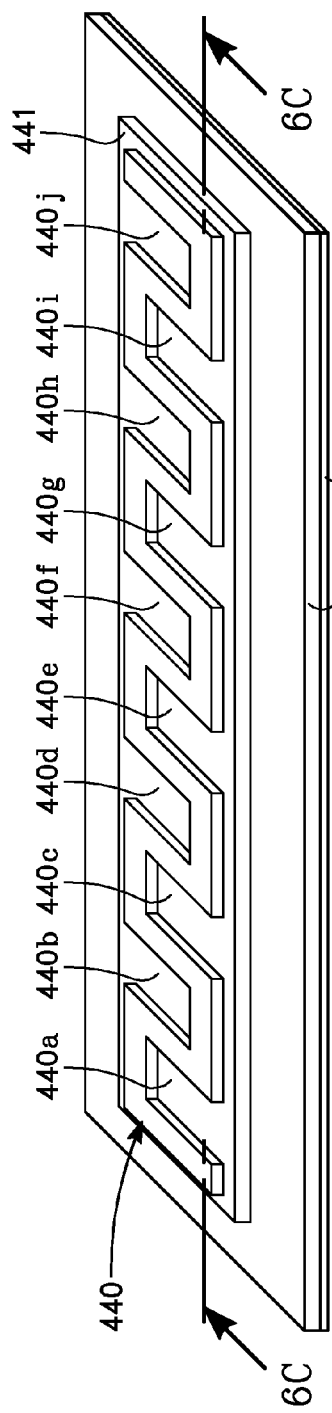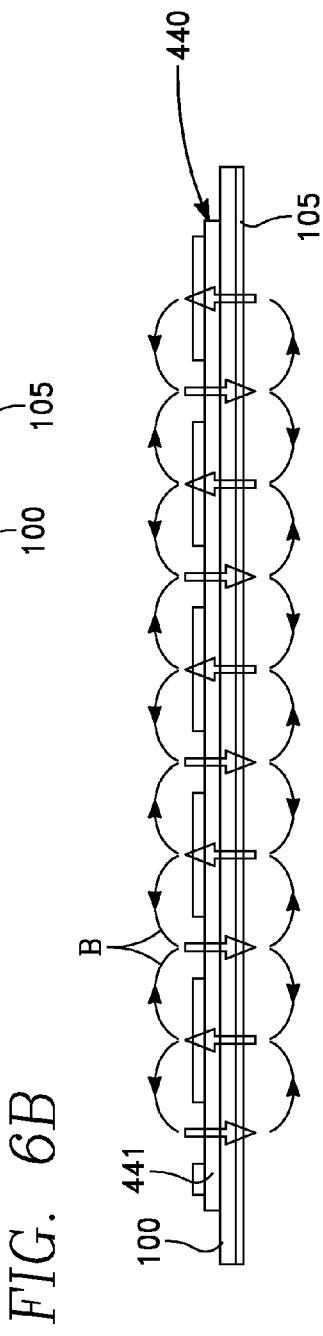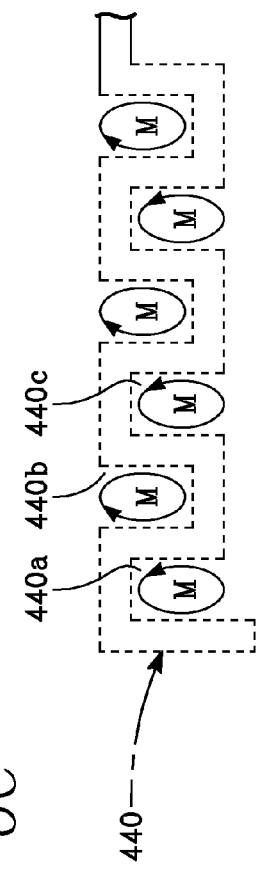

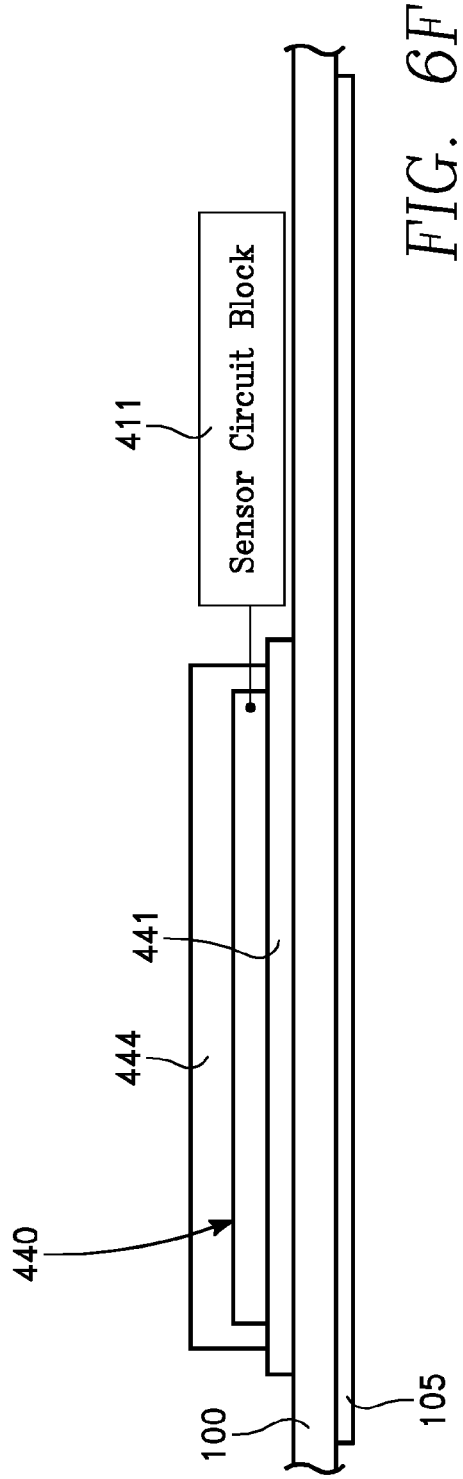
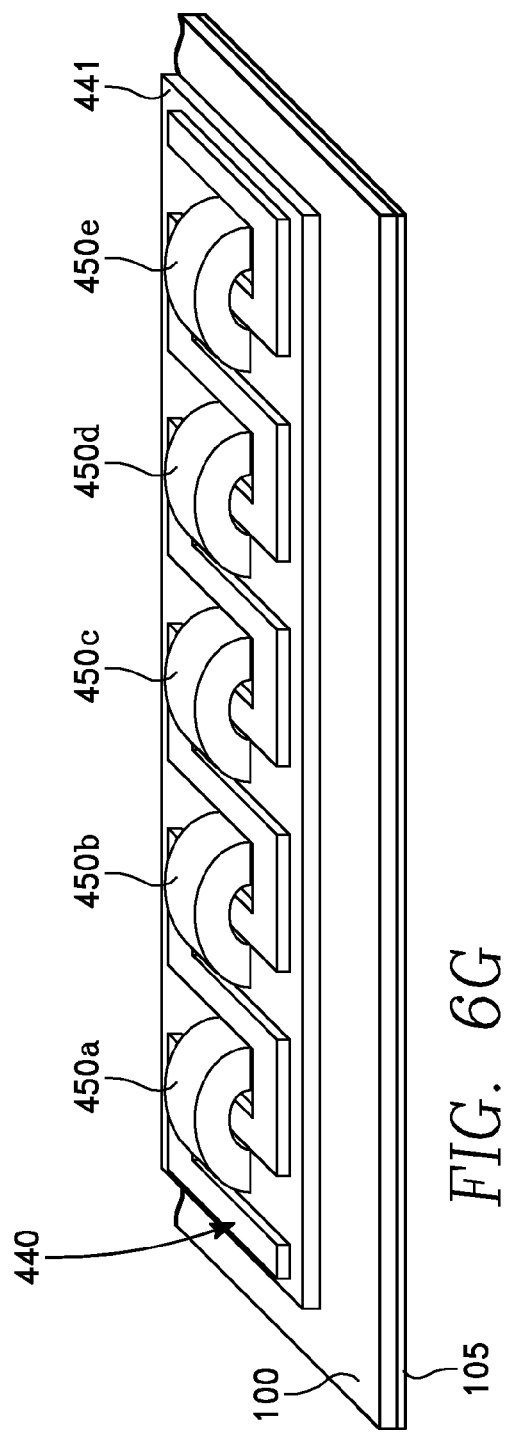

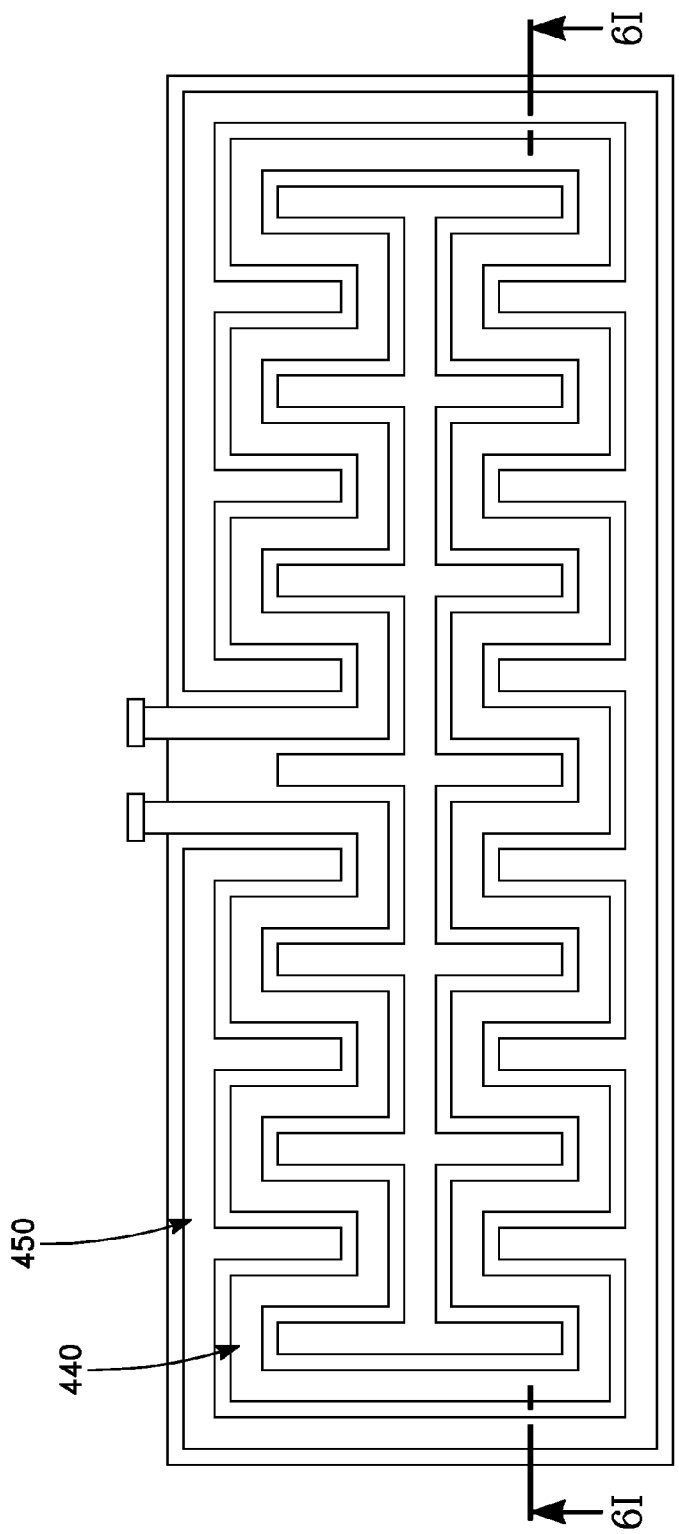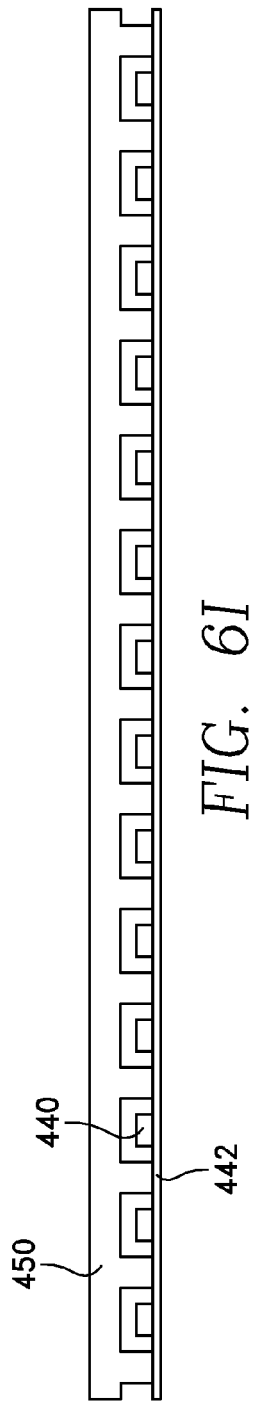
FIG. 6H
FIG. 6I

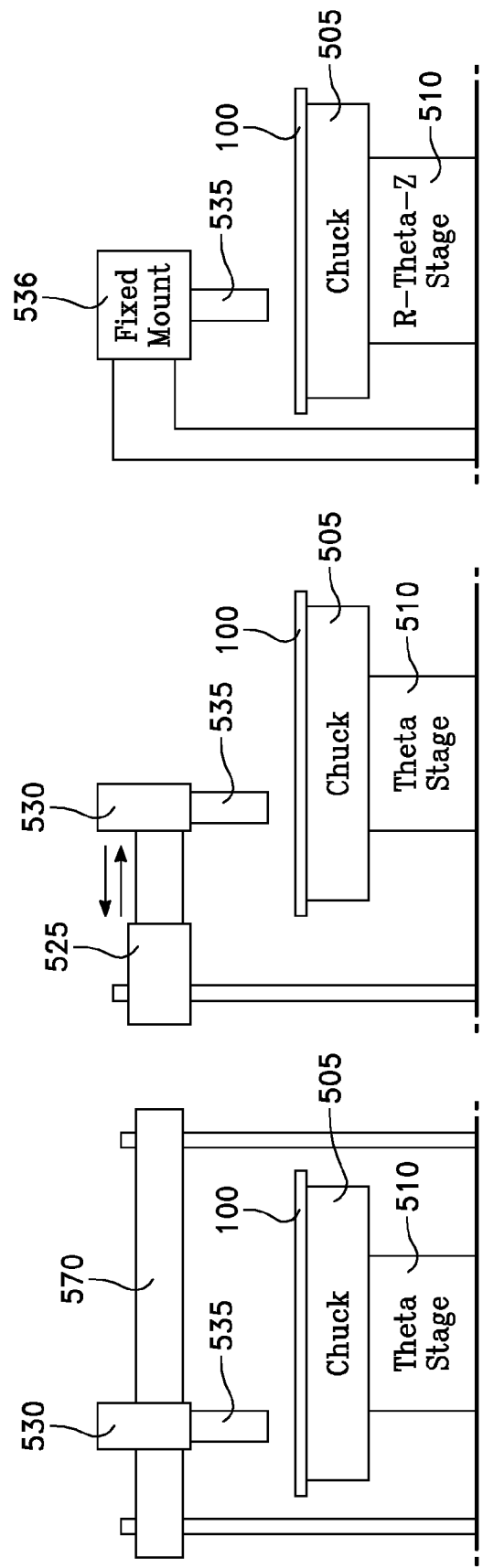

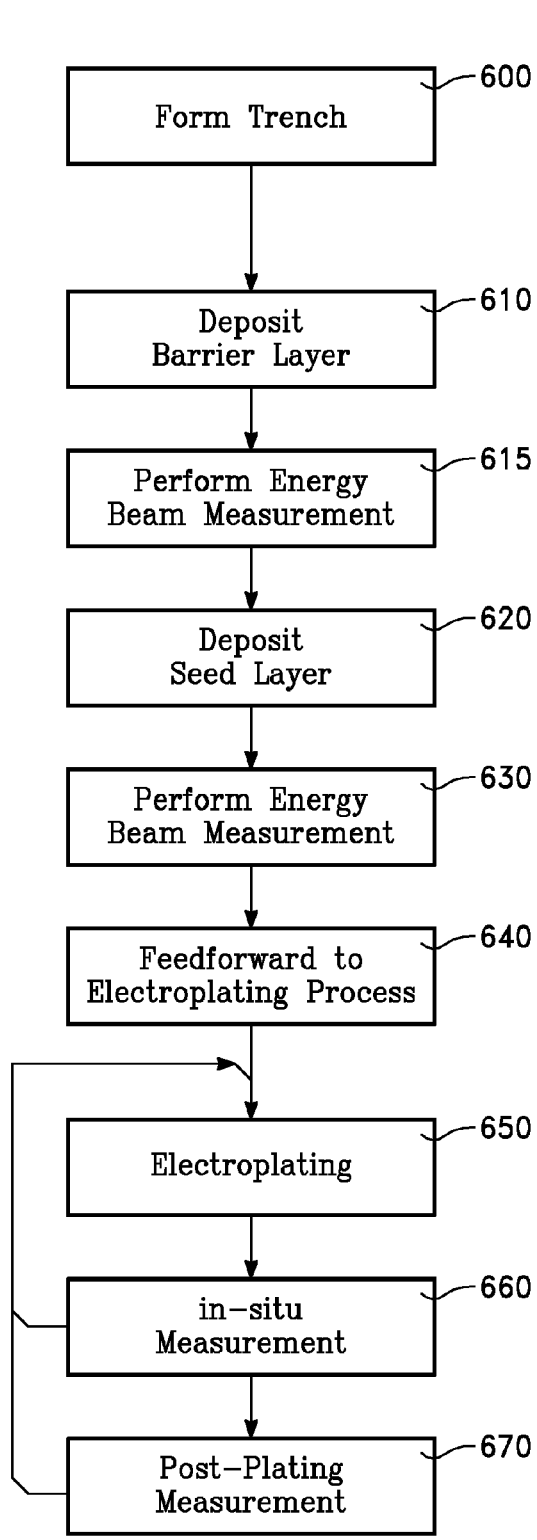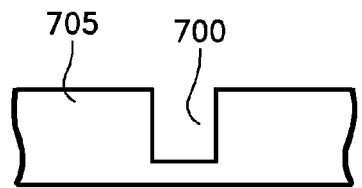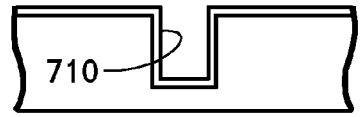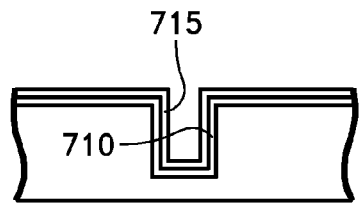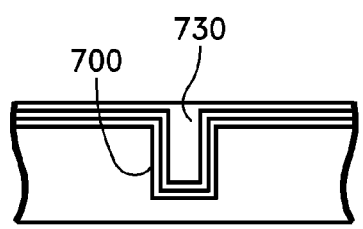
FIG. 17A
FIG. 17B
FIG. 17C
FIG. 17D
FIG. 16

NON-CONTACT SHEET RESISTANCE MEASUREMENT OF BARRIER AND/OR SEED LAYERS PRIOR TO ELECTROPLATING

CROSS-REFERENCE TO RELATED APPLICATIONS

This application claims benefit of U.S. Provisional Application Ser. No. 61/834,353, filed Jun. 12, 2013 entitled NON-CONTACT SHEET RESISTANCE MEASUREMENT OF BARRIER AND/OR SEED LAYERS PRIOR TO ELECTROPLATING, by Abraham Ravid, et al., which is herein incorporated by reference.

BACKGROUND

Technical Field:

The disclosure is related to processes and apparatus for forming conductive films on a workpiece such as a semiconductor wafer, and in particular for measuring and controlling uniformity in such films.

Background Discussion:

Semiconductor integrated circuits have conductive structures defined by trenches filled with a metal such as copper deposited on a barrier layer formed on or over the semiconductor or dielectric substrate. Copper migration into the semiconductor or dielectric substrate is prevented by forming the barrier layer of a suitable material such as tantalum nitride or titanium nitride, for example. Prior to filling the trench with copper, a thin copper seed layer is grown on the barrier layer by physical vapor deposition. Thereafter, a thick copper layer is deposited over the copper seed layer by electroplating, the thick copper layer being sufficient to fill the trench.

One problem with such processes is that non-uniformities in the spatial distribution of sheet resistance of the barrier layer and/or of the seed layer lead to corresponding non-uniformities in the spatial distribution of thickness in the copper layer formed by electroplating. Typically, sheet resistance in the underlying seed/barrier layer affects the electroplating deposition rate and surface compliance.

A related problem is that thickness sensors, such as eddy current (magnetic field loss) measurement sensors are employed to measure thickness, but typically only after completion of the electroplating process forming the thick copper layer. Generally, eddy current sensors are not suitable for reliable and sufficiently accurate thickness measurements of thin layer such as the barrier and seed layers (whose combined thickness is typically on the order of only 50-200 Angstroms). As a result, non-uniformities in copper layer thickness distribution (or electrical properties distribution) are not discovered until later, and the affected product wafers must be discarded. Any remedial measures are taken with reference to the next batch of wafers in the best case.

SUMMARY

A measurement tool for measuring an electrical parameter of a metal film deposited on a front side of a workpiece, includes a workpiece support, a contact ring facing the workpiece support and comprising at least one contact rod, a sensor connected to the at least one contact rod, a beam source having an energy beam propagation direction toward the front the of the workpiece corresponding to a beam impact location on the front side, a holder and a translation mechanism capable of translating the holder relative to the workpiece support, the beam source supported on the holder, and a computer coupled to an output of the sensor.

In one embodiment, the computer is connected to the beam source and to the translation mechanism. In another embodiment, the contact ring comprises plural contact rods arranged in a circle coinciding with an annular zone of the workpiece and coupled to the sensor. In a related embodiment, plural respective switches are connected between respective ones of the plural contact rods and the sensor. The switches may be electrically isolated from one another and controlled by the computer.

In an embodiment, the computer is programmed to enable different ones of the switches in successive times, and select different beam impact locations for different ones of the times by controlling the translation mechanism.

In one embodiment, the beam source produces a pulsed beam and the computer is programmed to sense a decay behavior of an output of the sensor during an off time of the pulsed beam. In another embodiment, the beam source produces a continuous beam, and the computer is programmed to sense a magnitude of an output of the electrical sensor.

In a further embodiment, the beam source comprises a light source, the reactor further comprising an anode electrode facing the workpiece support and a voltage supply connected to the anode electrode. In a related embodiment, a vacuum enclosure encloses the workpiece support and the path of the beam source.

In accordance an embodiment, a method of measuring spatial distribution of an electrical parameter of a metal film deposited on a surface of a workpiece includes: (a) selecting successive electrical return contacts at respective contact locations on the metal film, (b) directing an energy beam to respective beam impact locations on the metal film, respective ones the contact locations defining with respective ones of the beam impact locations respective current paths in the metal film, and (c) observing respective electrical responses in the respective current paths and inferring from the respective electrical responses respective values of the electrical parameter for the respective paths.

In one embodiment, the energy beam comprises a pulsed energy beam and the observing respective electrical responses is performed during respective off times of the pulsed energy beam. In another embodiment, the energy beam comprises a continuous energy beam and the observing respective electrical responses comprises observing respective magnitudes of the respective electrical responses.

In an embodiment, successive beam impact point locations are selected while the selected one of the return contact locations is held constant. In another embodiment, successive return contact locations are selected while the beam impact location is held constant.

One embodiment further comprises inferring a spatial distribution of the electrical parameter by correlating successive values of the electrical parameter with the corresponding paths.

In accordance with yet another embodiment, a method of operating an electroplating tool comprising separate electroplating anodes for depositing an overlying metal layer on an underlying metal film previously deposited the workpiece, includes: (a) observing respective responses to an energy beam along respective current paths in the metal film, inferring from the respective responses respective values of an electrical parameter, and deducing from the respective values a spatial distribution of the electrical parameter, and (b) adjusting a distribution of anode voltages among the separate anodes to compensate for a non-uniformity in the spatial distribution.

In one embodiment, the observing comprises: (a) providing an electrical return contact at a contact location on the metal film; (b) directing the energy beam to a selected beam impact location on the metal film, the beam impact location and the electrical return contact defining a path between them; (c) observing a respective value of the electrical parameter for the path; and (d) moving the contact location to successive contact locations and moving the beam impact location to successive beam impact locations to define different paths, and repeating (c) for each one of the paths.

In a related embodiment, the method further comprises inferring the spatial distribution of the electrical parameter in the metal film by correlating the respective values of the electrical parameter with the corresponding paths.

BRIEF DESCRIPTION OF THE DRAWINGS

So that the manner in which the exemplary embodiments of the present invention are attained can be understood in detail, a more particular description of the invention, briefly summarized above, may be had by reference to the embodiments thereof which are illustrated in the appended drawings. It is to be appreciated that certain well known processes are not discussed herein in order to not obscure the invention.

FIG. 3B is an elevational view corresponding to FIG. 3A and FIG. 3C is a plan view of an anode electrode of the embodiment of FIG. 3A.

FIGS. 6B-6J depict aspects of an eddy current sensor having a planar inductor adapted for use in the embodiment of FIG. 6A, of which FIGS. 6B, 6C and 6D are respective views of an embodiment of the planar inductor, FIGS. 6E and 6F are different views of the eddy current sensor including a planar inductor, FIG. 6G depicts a modification of the embodiment of FIG. 6E including ferrite cores, FIG. 6H depicts a modification having an integral ferrite core layer, FIG. 6I is a cross-sectional elevational view taken along lines 6I-6I of FIG. 6H, and FIG. 6J depicts an embodiment having a rectangular spiral.

FIGS. 12, 13 and 14 are plan views of alternative embodiments corresponding to FIG. 8.

FIG. 16 is a sequential block diagram of a process performed in the system of FIG. 15.

FIGS. 17A through 17D are sequential diagrams depicting changes in thin film structure on a workpiece during corresponding steps in the process of FIG. 16.

Figure 1A:
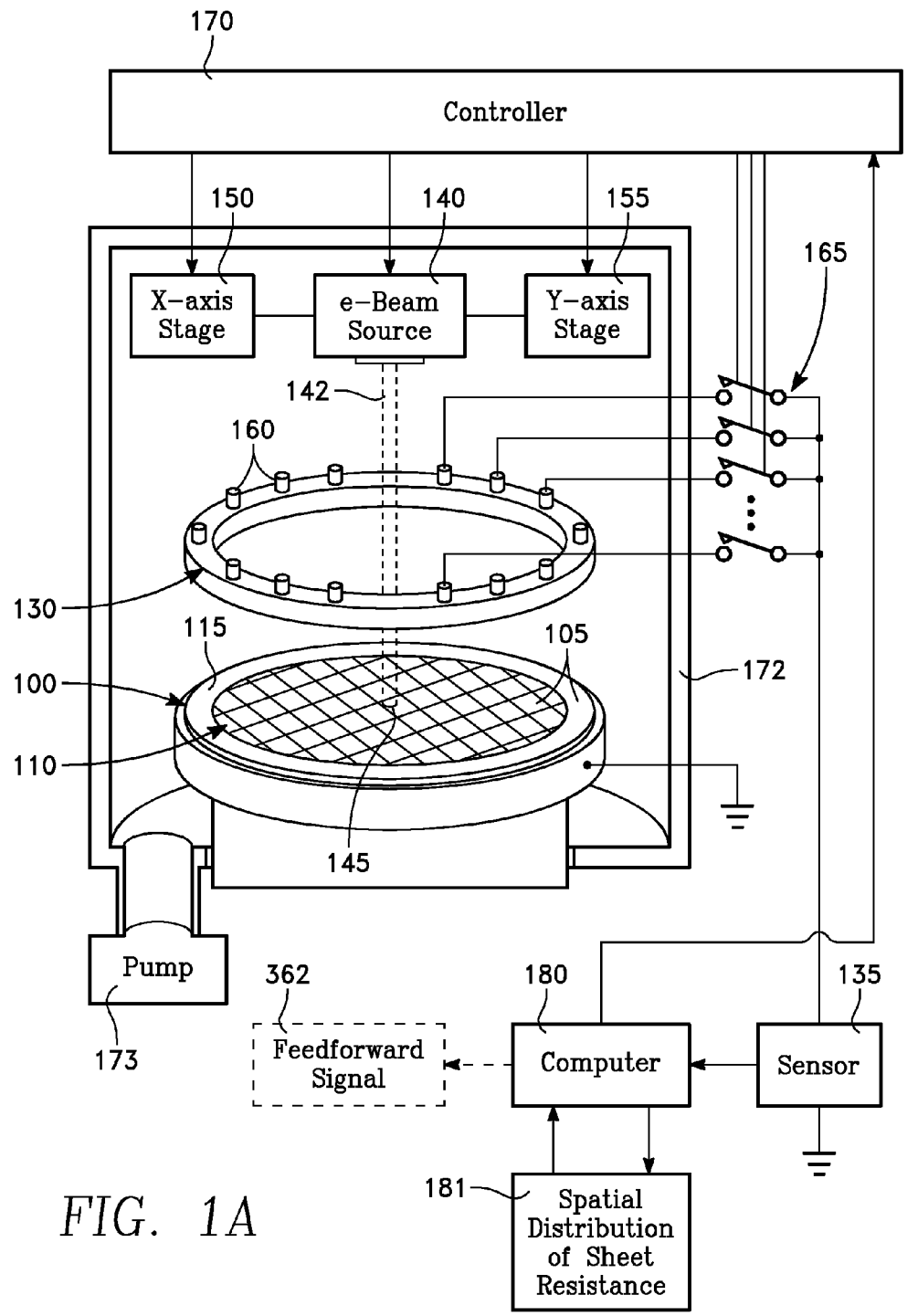
FIG. 1A includes a block diagram depicting an energy beam resistivity measurement tool in accordance with an embodiment.

To facilitate understanding, identical reference numerals have been used, where possible, to designate identical elements that are common to the figures. It is contemplated that elements and features of one embodiment may be beneficially incorporated in other embodiments without further recitation. It is to be noted, however, that the appended drawings illustrate only exemplary embodiments of this invention and are therefore not to be considered limiting of its scope, for the invention may admit to other equally effective embodiments.

DETAILED DESCRIPTION

Figure 1B:
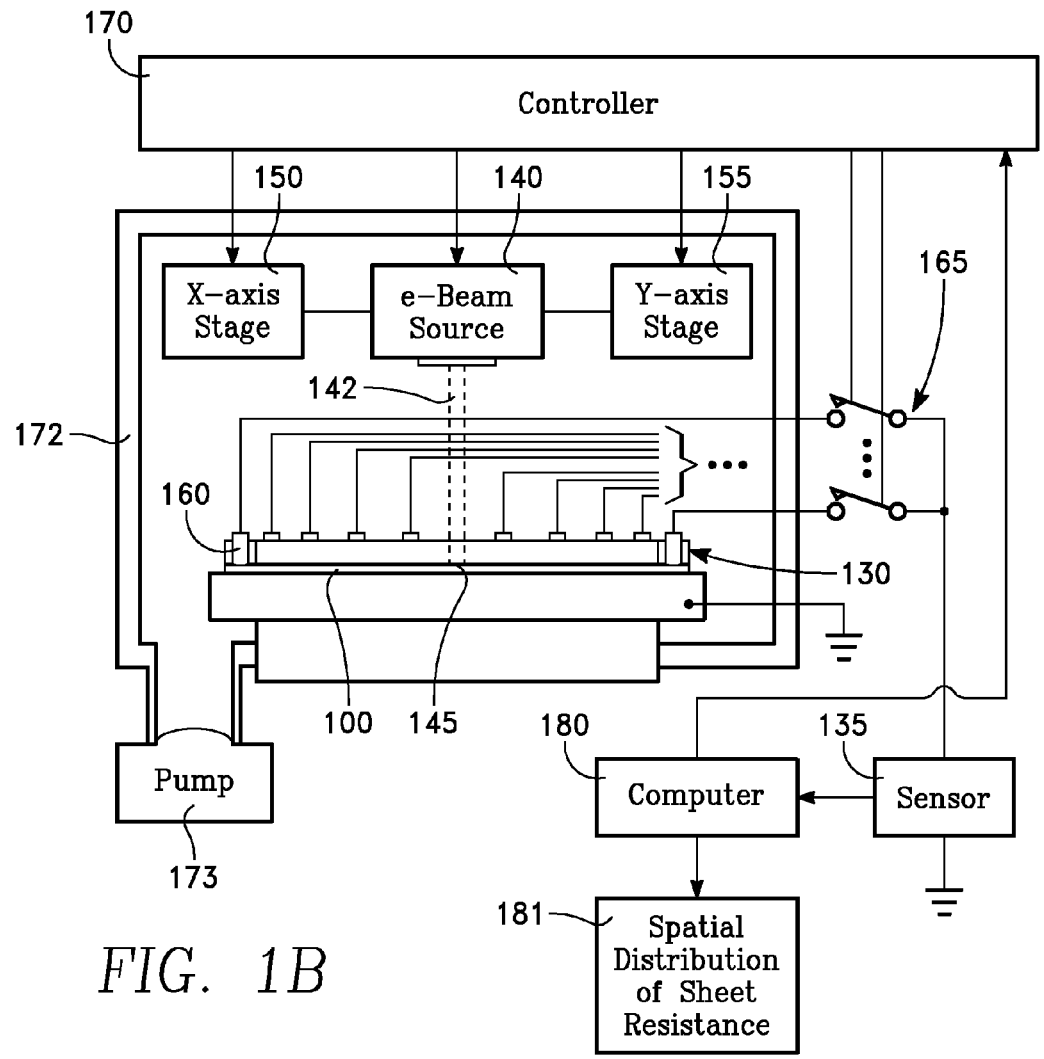
FIG. 1B includes an elevational view corresponding to FIG. 1A.
Figure 1C:
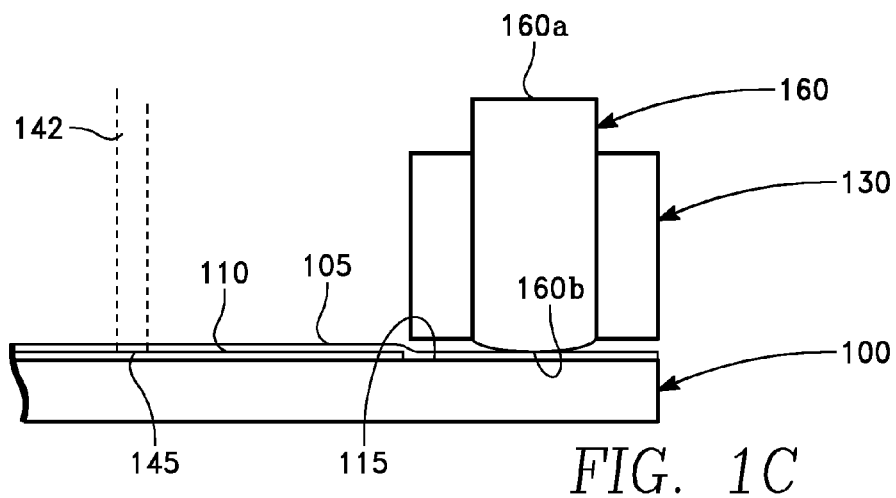
FIG. 1C is an enlarged elevational view of a portion of the tool of FIG. 1B.

Contactless Sheet Resistance Distribution Measurement:

FIGS. 1A, 1B and 1C depict a measurement tool employing an electron beam for measuring a material characteristic (such as sheet resistance) in barrier and seed layers prior to electroplating. Referring to FIGS. 1A-1C, a workpiece such as a semiconductor wafer 100 has a top surface including a main region 110 in which are formed integrated circuit structures, and a peripheral contact belt 115 as an annular zone at the wafer periphery surrounding the main region 110 and having a smooth topology devoid of any circuit structures. A metal layer 105 covers the main region 110 and the peripheral contact belt 115. Typically, the metal layer 105 can include a barrier layer of tantalum nitride or titanium nitride and a copper seed layer grown by physical vapor deposition on the barrier layer. The wafer 100 depicted in FIGS. 1A-1C has not undergone the electroplating process, and therefore the metal layer 105 is thin, on the order of 50-200 Angstroms, the combined thickness of the barrier and seed layers. The measurement tool of FIGS. 1A-1C facilitates a measurement of the spatial distribution of sheet resistance of the metal layer 105 across the top surface of the wafer 100. Because the metal layer 105 is very thin, such a measurement may be impractical if carried out using an eddy current sensor.

In one mode, the measurement tool of FIGS. 1A-1C employs an electron beam. A material characteristic (such as sheet resistance for example) is measured by observing an electrical parameter. In one embodiment, the electron beam is a pulsed beam, and the observed electrical parameter is the decay time of a current generated in the metal layer 105 during the off time between successive pulses of the electron beam. In another mode, the tool of FIGS. 1A-1C employs a continuous electron beam source, and the observed electrical parameter is the amplitude of the electrical response (e.g., voltage or current) in the wafer. As will be described below, different measurements may be made along different current paths in the metal layer 105.

Electrical contact is made to the peripheral contact belt 115 on the periphery of the wafer 100 in any suitable manner. For example, one manner of making such electrical connection is to hold a contact ring 130 on the peripheral contact belt 115 of the wafer 100. The contact ring 130 is an annulus coupled to an electrical reference potential (e.g., ground) through an electrical sensor 135, which may be a voltage sensor or a current sensor, for example. A beam source 140 is suspended over the top surface of the wafer 100, and produces an electron beam 142 that strikes the wafer 100 at a beam impact point 145. The wafer 100 acts as an anode and may be grounded, collecting electrons from the electron beam 142. Actuators including an X-axis stage 150 and a Y-axis stage 155 control a two-dimensional location of the beam source 140 in a plane parallel with the wafer top surface. In one embodiment, the diameter of the beam source 140 is sufficiently small to avoid interference with movement of the beam source 140 by the X-axis stage 150 and the Y-axis stage 155, permitting movement of the beam impact point 145 across the diameter of the wafer 100. In one embodiment, the contact ring 130 contacts the peripheral contact belt 115 through discrete electrically separate pointed contact rods 160 provided on the contact ring 130 and distributed circumferentially on the contact ring 130. As shown in FIG. 1C, each contact rod 160 has an upper portion 160a above the contact ring 130 and a lower portion 160b contacting the wafer 100 below the contact ring 130. Respective switches 165 are connected in series between the respective contact rods 160 and the electrical sensor 135. A controller 170 governs the switches 165 and governs the pulsing of the beam source 140 in a pulsed mode of operation. In one embodiment, the wafer 100 and the electron beam 142 are enclosed in a vacuum enclosure 172 evacuated by a vacuum pump 173.

The electron beam 142 generates an electrical current in the metal layer 105 that flows from the point of the beam impact point 145 to ground through the contact ring 130 and the electrical sensor 135.

If the beam source 140 is operated in a pulsed mode, then at the end of each beam pulse, this current decays at a rate determined (at least in part) by the resistance and capacitance in the path followed by the current. If the decay is an exponential function, then the time in which the current decays from an initial magnitude to a fraction 1/e of that initial magnitude is function of the resistance R, inductance L and the capacitance C of the path followed by the current. The effect of the inductance L is typically negligible, and the decay time is principally determined by R and C, and may be referred to as the RC decay time. A computer 180 coupled to the electrical sensor 135 deduces the time-domain waveform of the output of the electrical sensor 135 (e.g., the RC decay time), which is the observed electrical parameter. From this electrical parameter, the computer 180 computes the value of a material characteristic (e.g. sheet resistance) of the current path in the metal layer 105, in accordance with well-known principles.

In one embodiment, the controller 170, governed by the computer 180, enables a single one of the switches 165 during (and slightly after) each pulse, and may enable different switches 165 during successive pulses. The controller 170 also changes the location of the impact point 145 of each pulse by controlling the X- and Y-axis stages 150, 155. Thus, the current path for each pulse is precisely established between an X-Y location of the impact point 145 and one of the contact rods 160 corresponding to the one switch enabled during the current pulse. Over the course of numerous pulses of the pulsed electron beam 142, the X-Y location of the beam impact point 145 and the chosen contact rod 160 may be changed in any sequence determined by the computer 180. By thus changing the electrical paths for successive pulses, the computer 180 can deduce a spatial distribution of the electrical characteristic (e.g., sheet resistance) over a number of pulses.

In one embodiment, the electron beam source is operated in the CW (continuous) mode, and the observed electrical parameter is the raw magnitude of the electrical response (e.g., a D.C. voltage or current) sampled at the electrical sensor 135. The computer 180 infers from this raw magnitude a value of the material characteristic of interest (e.g., sheet resistance). This inference may be made by comparing the raw magnitude with results previously obtained in calibration samples whose material characteristic (e.g., sheet resistance) is known. A tabulation of the results of many such calibration samples covering a desired range of values may be accessed by (or stored in) the computer 180, for rapid translation of measurements on a production wafer. In one embodiment of this mode, the beam impact point 145 and the selection of one of the contact rods 160 are changed to establish different current paths, and respective measurements of the electrical parameter are obtained for respective paths.

Figure 2A:
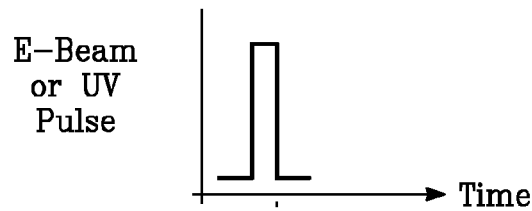
FIGS. 2A and 2B are contemporaneous time domain waveforms depicting, respectively, a single energy beam pulse and a corresponding current sensor response in the embodiment of FIGS. 1A through 1C.
Figure 2B:
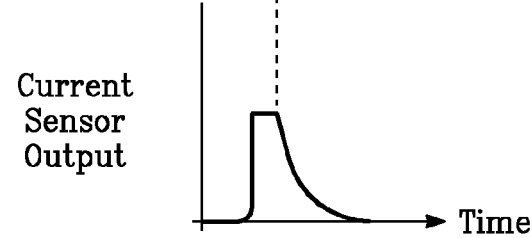

For an embodiment in which the beam source 140 is a pulsed beam source, FIG. 2A depicts a single pulse by the pulsed beam source 140, while FIG. 2B depicts a time domain waveform of current in the metal layer 105 of FIG. 1A generated by that pulse, as sensed by the electrical sensor 135.

Figure 1D:
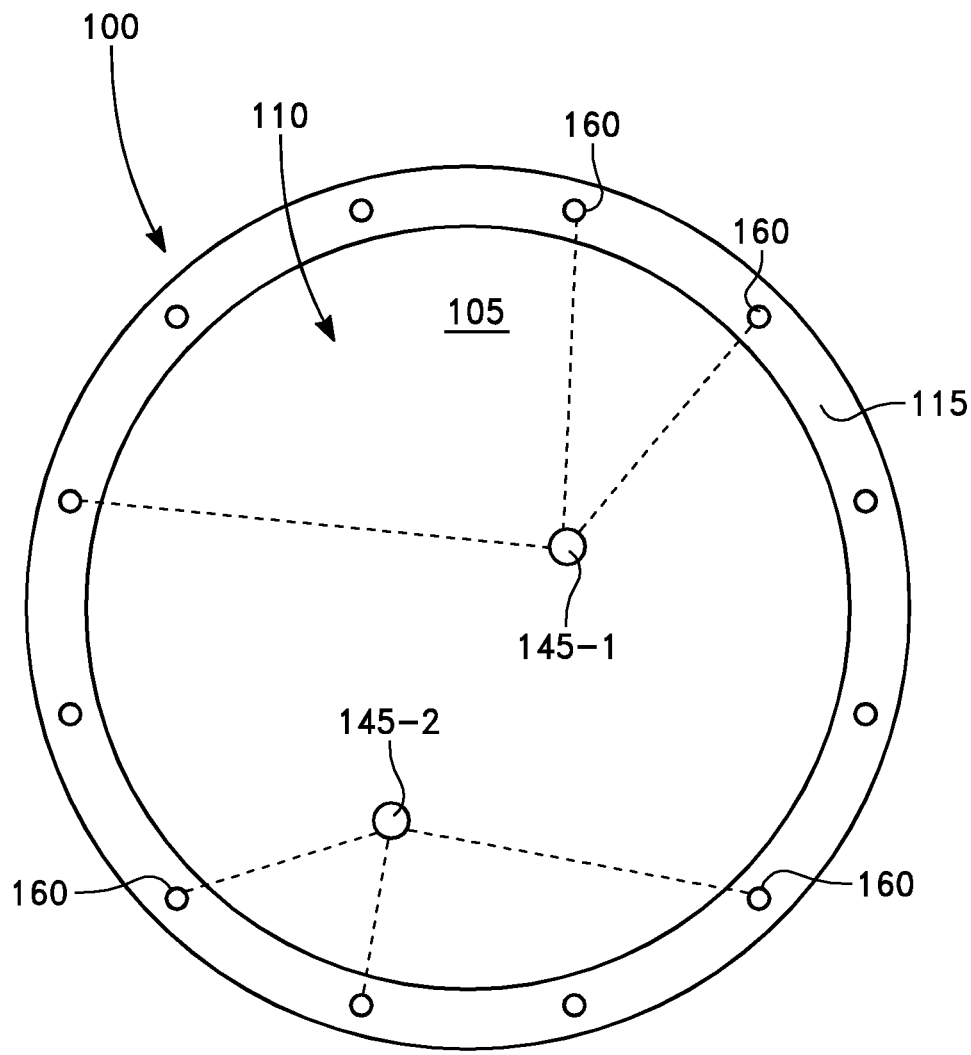
FIG. 1D is a plan view of a workpiece and points of contact by a contact ring in the embodiment of FIGS. 1A through 1C.
Figure 2C:
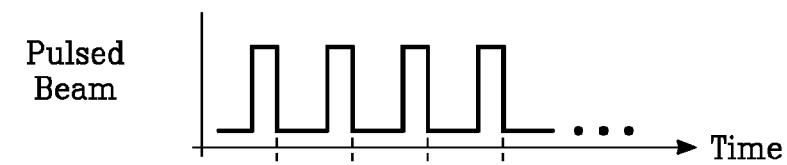
FIGS. 2C, 2D and 2E are contemporaneous time domain waveforms of, respectively, a succession of energy beam pulses, a corresponding current sensor output and an angular position of a currently enabled contact rod in the embodiment of FIGS. 1A through 1C.
Figure 2D:
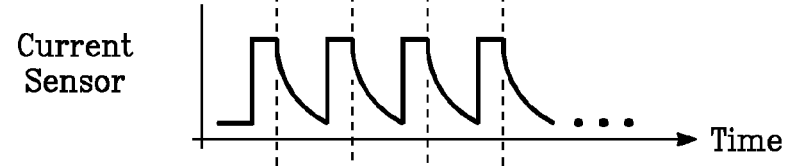
Figure 2E:
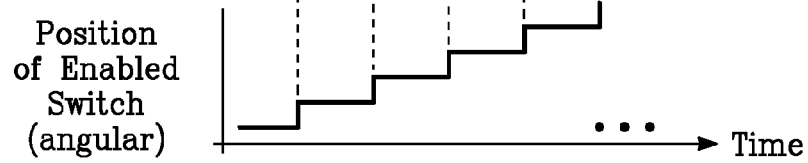

FIG. 2C depicts a succession of pulses from the beam source 140, FIG. 2D depicts a succession of responsive currents generated in respective current paths by the pulses, and FIG. 2E depicts the angular location of the enabled switch during each successive pulse of FIG. 2C in accordance with one example. In FIG. 2E, the beam impact point 145 may be held constant for a selected number of pulses during which different contact rods 160 are selected. Thereafter, the X- and Y-axis stages 150, 155 may operate to shift the location of the impact point 145, and the procedure may then be repeated. One example is depicted in FIG. 1D, depicting the peripheral contact belt 115 of the wafer 100 and its points of contact with the contact rods 160. FIG. 1D further shows an example of different beam impact points 145-1, 145-2 on the wafer 100, with different contact rods 160 being selected for each to establish different current paths. In one embodiment, for example, one beam impact point 145-1 may be at an inner radius, while another beam impact point 145-2 may be at an outer radius. Each beam impact point may receive a number of beam pulses, with a different ones of the contact rods 160 being enabled at different times to establish a different current path. In this manner, a model of the radial distribution of sheet resistance may be constructed by the computer 180 (FIG. 1A) so that radial non-uniformity in sheet resistance distribution may be deduced by the computer 180. Such information constructed by the computer 180 may be furnished as a feed forward correction to an electroplating process to be performed on the wafer 100.

Figure 3A:
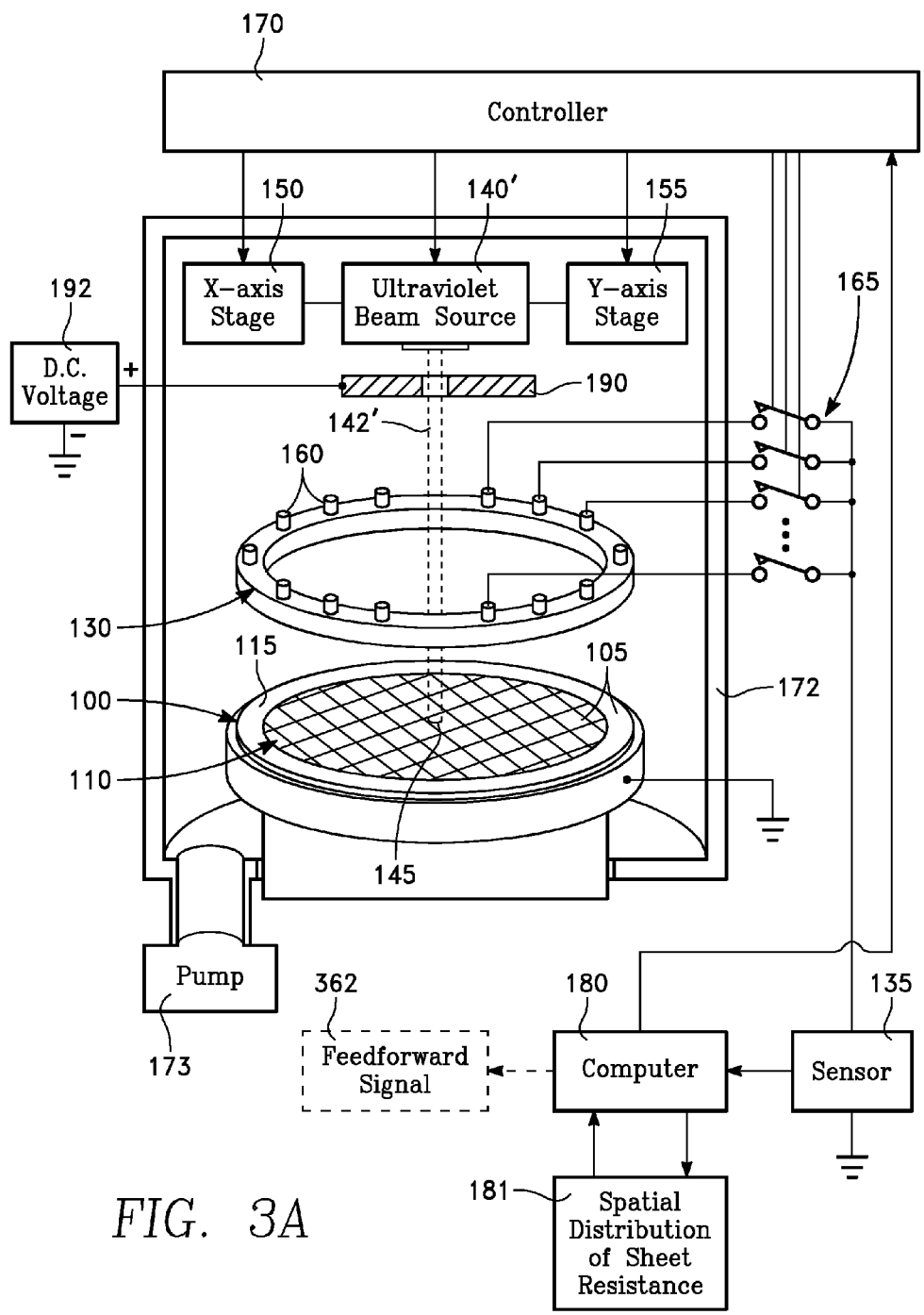
FIGS. 3A, 3B and 3C depict an alternative embodiment employing a light beam source, of which FIG. 3A includes a block diagram.
Figure 3B:
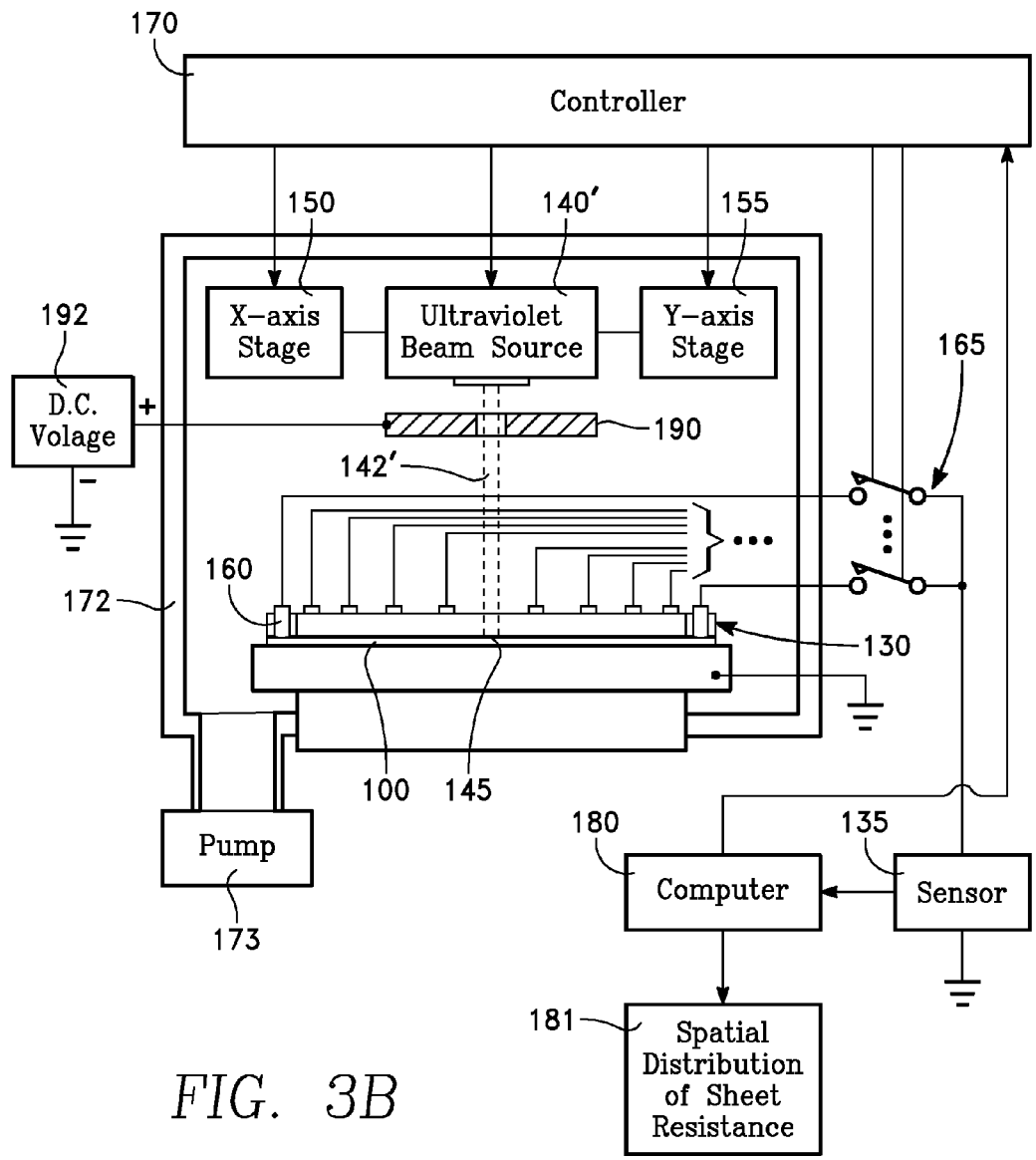
Figure 3C:
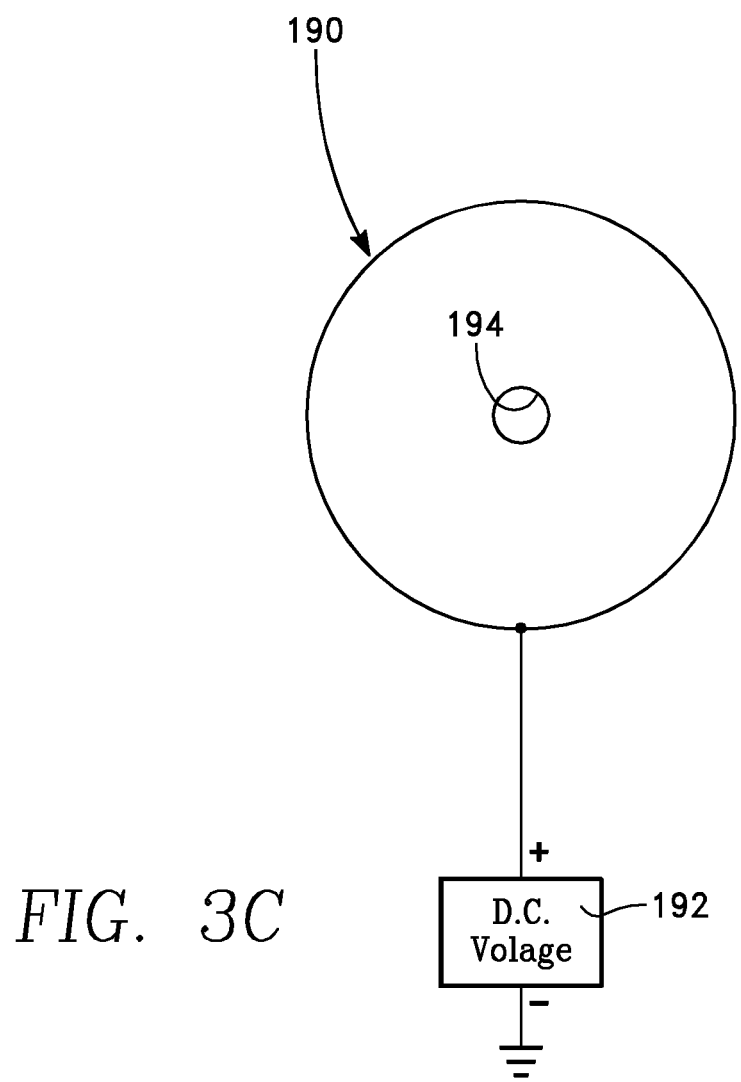

FIGS. 3A and 3B depict a modification of the embodiment of FIGS. 1A and 1B, in which the beam source 140 (i.e., the electron beam source) is replaced by a high energy (e.g., ultraviolet) light beam source 140', which generates a light beam 142'. The optical frequency of the light beam 142' in one embodiment corresponds to a photon energy exceeding the work function of the metal layer 105. A small overhead anode electrode 190 provided within the vacuum enclosure 172 to capture electrons emitted from the metal layer 105 due to interaction with the light beam 142'. In one embodiment, the anode electrode 190 is mechanically coupled to the light beam source 140', and follows movements of the light beam source 140' controlled by the X-axis stage 150 and Y-axis stage 155. In one embodiment, the diameter of the anode electrode 190 is sufficiently small to avoid interference with movement of the light beam source 140' by the X-axis stage 150 and the Y-axis stage 155, permitting movement of the beam impact point 145 across the diameter of the wafer 100. The anode electrode 190 is connected to the positive terminal of a D.C. voltage source 192, whose negative terminal is connected to ground. The wafer 100 acts as a cathode in this embodiment. As depicted in FIG. 3C, the anode electrode 190 has a central hole 194 through which the light beam 142' passes.

The light beam source 140' in the embodiment of FIGS. 3A-3C may be either a pulsed beam source or a continuous beam source. The embodiment of FIGS. 3A-3C can include the other features of the embodiment of FIGS. 1A-1C. If the light beam source 140' is a pulsed beam source, then the desired measurement of a material characteristic (e.g., sheet resistance) is inferred from the behavior of the output of the electrical sensor 135 during successive pulsed beam off times, in the manner described above with reference to FIGS. 1A-1C. If the light beam source 140' is a continuous beam source, then the desired measurement of a material characteristic is inferred from the magnitude of the output of the electrical sensor 135, in the manner described above with reference to FIGS. 1A-1C.

Feed Forward Control of Electroplating Process:

In one embodiment, the computer 180 of FIG. 1A may be programmed to use many successive measurements of a material characteristic (e.g., sheet resistance) in the metal layer 105 along many different paths, to construct a distribution model 181 representing distribution of the material characteristic in the metal layer 105 across the wafer surface. In the remainder of this detailed description, the material characteristic is referred to as sheet resistance, although other material characteristics of the metal layer 105 may be measured instead. For example, the thickness of the metal layer 105 may be inferred from the sheet resistance. Thus, the distribution model 181 may represent distribution of any suitable characteristic of the metal layer, such as sheet resistance, thickness, or other characteristic. The distribution model 181 constructed by the computer 180 may be used by the computer 180 to produce a signal representing feed forward correction to an electroplating process in which a thick metal (copper) layer is formed over the thin metal layer 105 on wafer 100. The feed forward correction compensates for non-uniformity represented in the distribution model 181. For example, measurements of sheet resistance distribution in the metal layer 105 taken at the conclusion of the PVD process for barrier and seed layer deposition may be used to compensate for the measured non-uniformities during an electroplating process performed later on the same wafer.

Figure 4:
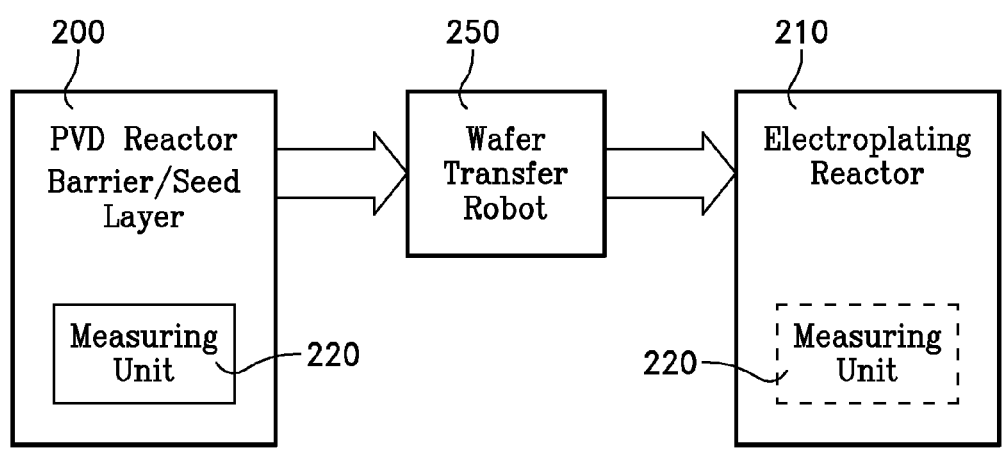
FIG. 4 is a schematic block diagram of an integrated system including the energy beam resistivity measurement tool of FIGS. 1A through 1C and an electroplating tool.

A system incorporating such feed forward process control is depicted in FIG. 4. A physical vapor deposition (PVD) reactor 200 is employed to deposit the thin (e.g., 50-200 Angstroms) barrier and copper seed layers referred to above. An electroplating tool or electroplating reactor 210 is employed to form a thick copper layer over the thin copper seed layer. An energy beam measurement tool 220 of FIG. 4 embodies the energy beam measuring apparatus of FIGS. 1A-1C. The energy beam measurement tool 220 may be included in the PVD reactor 200 (to measure a wafer upon completion of either the barrier and/or seed layer deposition step). Alternatively, the energy beam measurement tool 220 may be included in the electroplating reactor 210 in order to measure incoming wafers prior to performing the electroplating step. A wafer transfer robot 250 transports the wafers from the PVD reactor 200 to the electroplating reactor 210. The energy beam measurement tool 220 provides to the electroplating reactor 210 a feed forward signal representing or containing information regarding non-uniformity in the barrier and/or seed layer. The electroplating reactor 210 responds to the feed forward signal by adjusting radial distribution of the electroplating deposition rate.

Figure 5A:
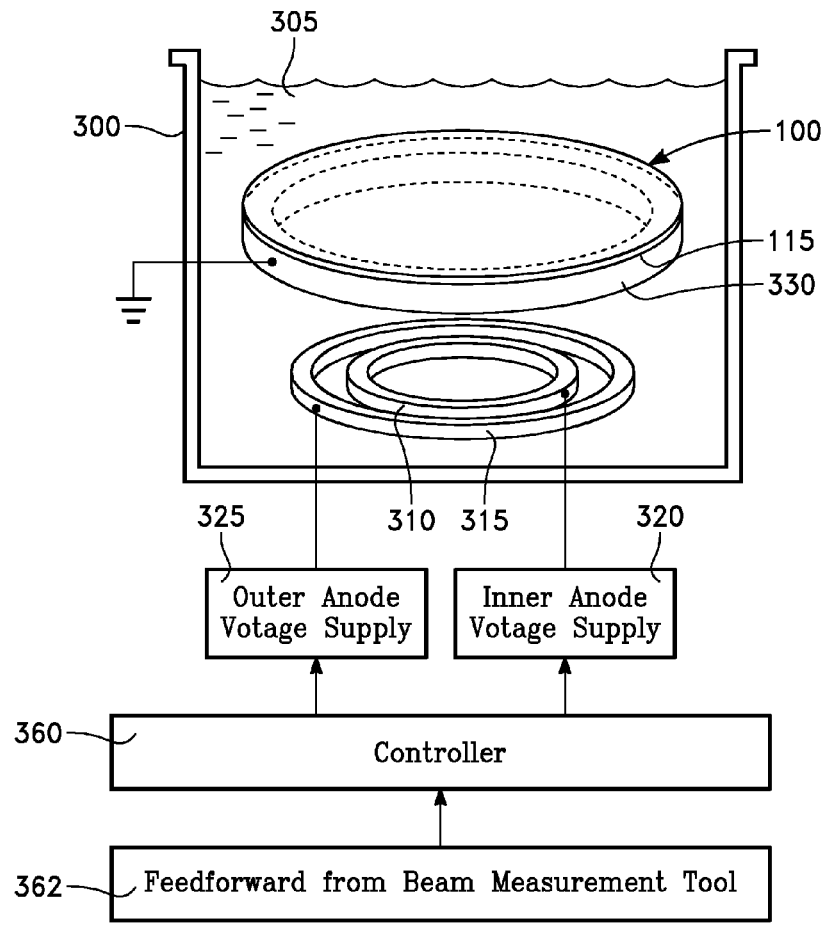
FIG. 5A includes an orthographic view depicting one embodiment of an electroplating tool in the integrated system of FIG. 4.
Figure 5B:
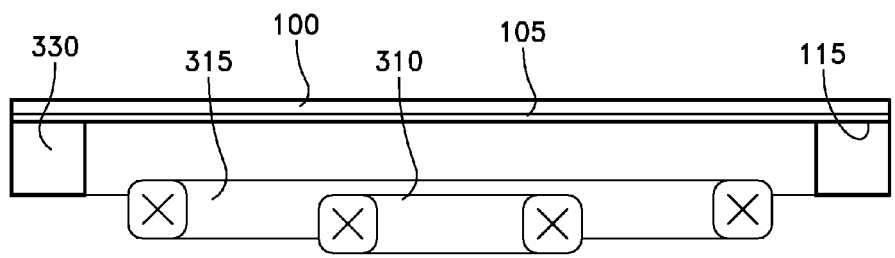
FIG. 5B is an elevational view of a portion of the embodiment of FIG. 5A.

An embodiment of an electroplating reactor that is capable of adjusting radial distribution of deposition rate is depicted in FIGS. 5A and 5B. The electroplating reactor of FIGS. 5A and 5B is used to form a thick metal (copper) layer over the metal layer 105 referred to previously with reference to FIG. 1C. The electroplating tool of FIGS. 5A and 5B includes a bath container 300 filled with a solution 305 such as a copper-containing liquid electrolytic solution (e.g., copper sulfate). Plural (e.g., at least two) anode rings 310, 315 immersed in the solution 305 are driven by respective anode voltage sources 320, 325. The anode rings 310, 315 may be concentric. The front side (only) of the wafer 100 (i.e., the side on which the integrated circuit structures are formed) is immersed in the solution 305 facing the anode rings 310, 315 and spaced from them. The back side of the wafer 100 is outside or above the solution 305. A cathode ring 330 contacts the peripheral contact belt 115 on the front side of the wafer 100 to provide a complete circuit for the electroplating current. In one embodiment, the cathode ring 330 supports the wafer 100, and may be grounded (or connected to a suitable return potential referenced to the anode voltage sources 320, 325). A controller 360 governs a voltage ratio between the anode voltage sources 320, 325 to control the radial distribution of the deposition rate of the electroplating process.

In one embodiment, the controller 360 receives a feed forward signal 362 from the energy beam measurement tool 220 shown in FIG. 4, which is of the type described with reference to FIG. 1A or 3A. The feed forward signal 362 is derived from the distribution model 181 of FIG. 1A or 3A, and represents the distribution of a chosen characteristic (e.g., sheet resistance or thickness) of the underlying barrier and seed layers. The controller 360 determines from the feed forward signal 362 a desired voltage ratio between the anode voltage sources 320, 325 to correct the non-uniformity. The controller 360 may be programmed to determine the optimum voltage ratio based upon non-uniformity in a measured distribution of sheet resistance. For example, an edge-high non-uniformity in radial distribution of sheet resistance may be compensated by a distribution of anode source voltages that is center-high (or edge-low). Conversely, a center-high non-uniformity in radial distribution of sheet resistance may be compensated by a distribution of anode voltages that is edge-high (or center-low).

Figure 6A:
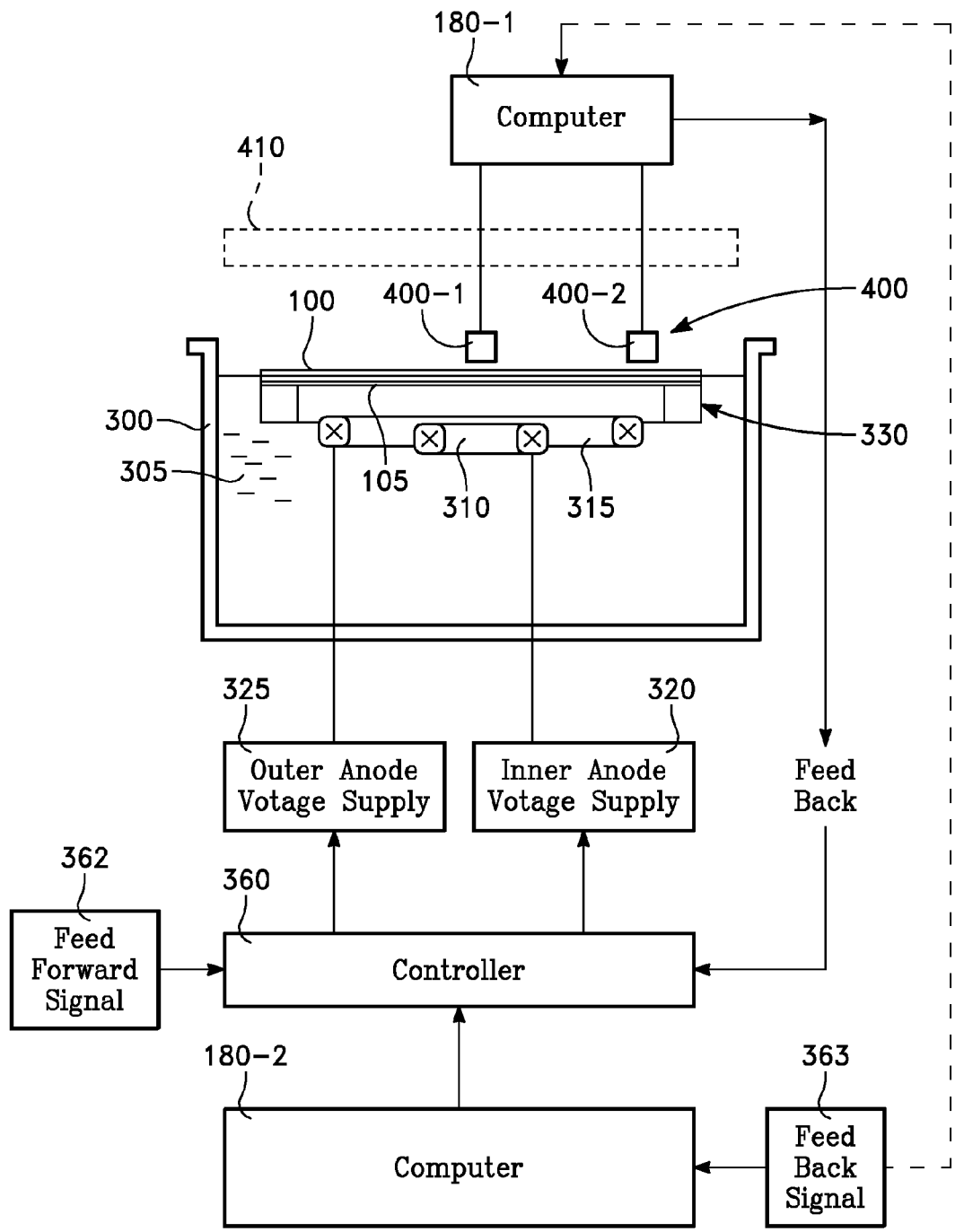
FIG. 6A includes an elevational view depicting one embodiment of an electroplating tool having internal sensors and feedback control.

In-Situ Feedback Control of the Electroplating Process:

FIG. 6A illustrates a modification of the embodiment of FIGS. 5A and 5B, in which feedback control of the electroplating process is provided in real time during the electroplating process based upon measurements continuously performed on the wafer. In the embodiment of FIG. 6A, the wafer 100 is held by the cathode ring 330 on the surface of the solution 305, so that only the front side of the wafer 100 (e.g., the side of the wafer 100 on which the integrated circuit structures are formed) is in the solution 305, while the back side of the wafer 100 is above (not immersed in) the solution 305. An array of plural sensors 400, such as plural eddy current loss measuring sensors (hereinafter referred to as eddy current sensors) are placed on the back side of the wafer 100. In one embodiment, the sensors 400 include a sensor 400-1 at a radially inner location and a sensor 400-2 at a radially outer location on the wafer back side. Each of the sensors 400 in the array is referred to generically as a thickness sensor. As employed in this specification, the term "thickness sensor" refers to any sensor, such as an eddy current sensor, capable of sensing a parameter affecting deposition rate or thickness in a metal plating process. This parameter may be sheet resistance, resistivity, conductance, conductivity or thickness itself. The thickness sensor has an output indicative of a measured value of the parameter.

A computer 180-1 periodically samples the output signals from the eddy current sensors 400-1 and 400-2 and deduces from the latest sample of those signals an instantaneous radial distribution of thickness of the deposited metal films. The computer 180-1 constructs, from the instantaneous radial distribution, a corrective feedback signal and sends it to the controller 360. This corrective signal represents a change in the voltage ratio between the anode voltage sources 320, 325 that compensates for the non-uniformity in radial thickness distribution deduced according to the latest sample.

Referring again to FIG. 6A, wafer handling apparatus 410, is disposed over the wafer 100 and restricts the space above the array of sensors 400 to a small vertical clearance. It is difficult to fit a conventional eddy current sensor into this restricted space. To overcome this problem, a very thin eddy current sensor employing a planar inductor is provided. Its structure may be implemented in each individual eddy current sensor 400-1, 400-2, etc., of the array of sensors 400. The planar inductor is depicted in FIGS. 6B and 6C as an elongate conductor 440 supported on a dielectric layer or substrate 441. The elongate conductor 440 will be referred to herein as the planar inductor 440. The planar inductor 440 forms a serpentine pattern defining rectangular serpentine loops 440a, 440b, 440c, etc. Each serpentine loop 400a, 400b, 400c, etc., is depicted as having a rectangular shape, although other shapes may be employed. The drawing of FIG. 6B depicts the planar inductor 440 as including ten serpentine loops 400a through 400j, although another number of serpentine loops may be employed.

In the embodiment of FIG. 6A, the wafer 100 is inverted to face down, and the front side of the wafer 100 is immersed in the solution 305 while the wafer back side is above the liquid surface of the solution 305. The eddy current sensor including the planar inductor 440 overlies the back side of the wafer 100 while the metal layer 105 is on the front (immersed) side of the wafer 100. In other uses in which the wafer is not inverted, the eddy current sensor may directly overlie the metal layer 105 on the wafer front side.

FIG. 6C depicts the magnetic fields B produced at successive portions of the planar inductor 440. FIG. 6D depicts the instantaneous eddy current loops M produced in the metal layer 105 at the respective serpentine loops 440a, 440b, 440c, etc. The planar inductor 440 of FIG. 6D produces plural eddy currents M distributed along its path in the underlying metal layer 105. In contrast, a conventional eddy current sensor employs a single multi-turn coil that produces a single eddy current loop in the underlying metal layer 105. The plural eddy currents M produced by the planar inductor 440 ensure a response to changes in thickness that is at least as great as that of the single multi-turn coil of a conventional sensor.

Figure 6E:
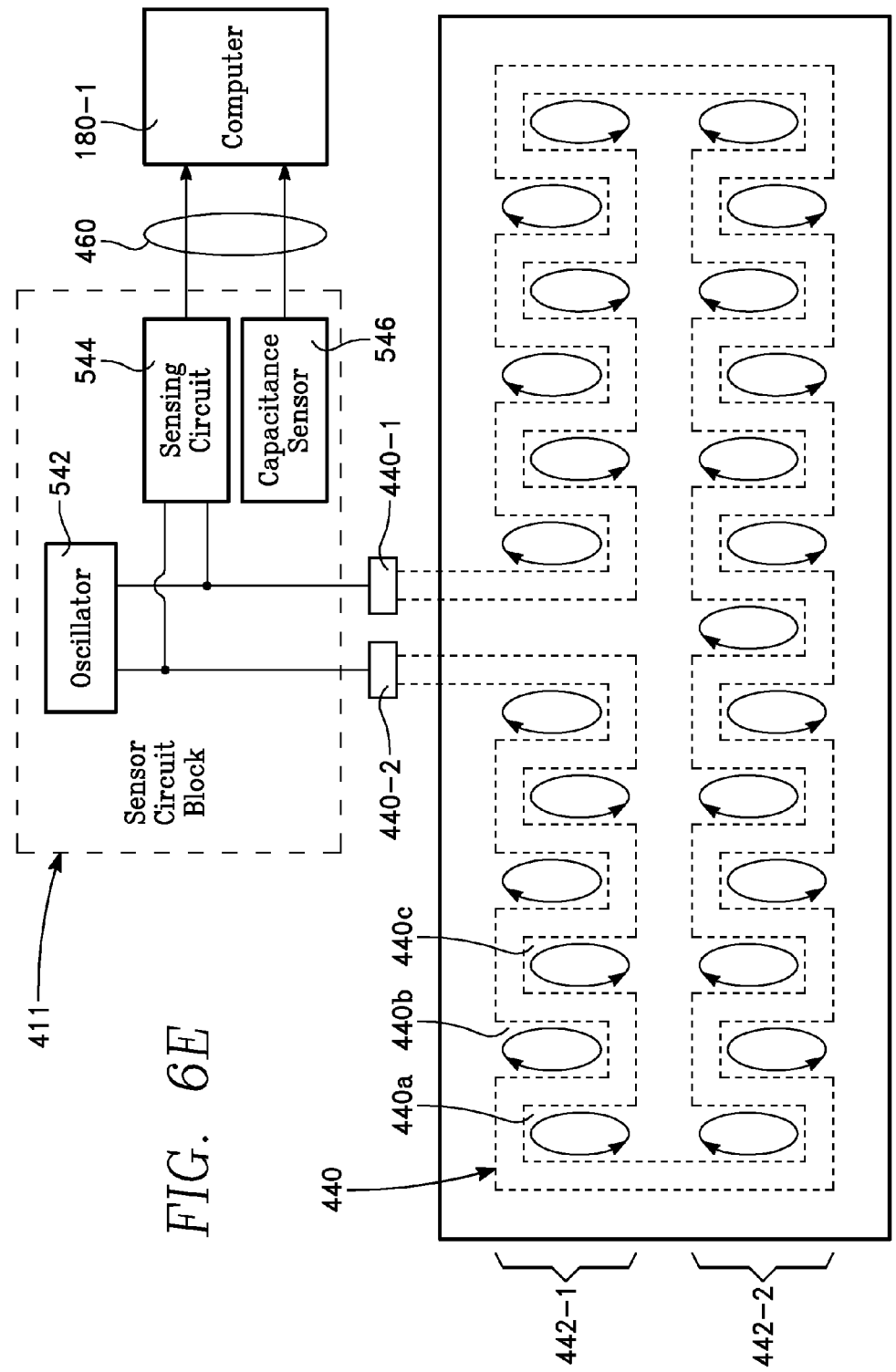

In the embodiment of FIG. 6E, the planar inductor 440 has a pair of end terminals 440-1, 440-2 which are adjacent one another. As shown in FIG. 6E, the planar inductor 440 forms a large circuit consisting of many serpentine loops 400a, 400b, 400c, etc., distributed along opposite directions from the pair of end terminals 440-1, 440-2. In the embodiment of FIG. 6E, the large circuit of the planar inductor 440 includes a pair of opposing serpentine row patterns 442-1 and 442-2 parallel to one another, to complete a circuit between the end terminals 440-1 and 440-2. While the row patterns 442-1, 442-2 of FIG. 6E form a rectangular sensor shape or footprint, the planar inductor 440 may be modified to form another sensor shape, which may be circular, elliptical or arcuate, for example.

As depicted in FIGS. 6E and 6F, the planar eddy current sensor includes a sensor circuit block 411 connected to the planar inductor 440. The sensor circuit block 411 may be thin as the planar inductor, and may be implemented as integrated circuitry. The sensor circuit block 411 includes an RF oscillator 542 driving the planar inductor 440, an impedance sensing circuit 544 coupled to the planar inductor 440, and a capacitance sensor 546. Both the impedance sensing circuit 544 and the capacitance sensor 546 have their outputs coupled to the computer 180-1 via a cable 460. Changes in thickness in the underlying metal layer 105 (FIG. 6A) change the RF impedance of the planar inductor 440, which is detected by the impedance sensing circuit 544, and may be translated by the computer 180-1 to a thickness measurement. The capacitance sensor 546 is a displacement sensor that monitors the lift-off distance or height of the planar inductor 440 above the metal layer 105 (FIG. 6A) under measurement. In one embodiment, the measured lift-off distance is used by the computer 180-1 to calibrate each measurement. In one embodiment, the bottom of the capacitance sensor 546 may be co-planar with the plane of the planar inductor 440.

FIG. 6F depicts the sensor of FIG. 6E in elevation, showing the planar inductor 440 as a conductive thin film, and the dielectric layer or substrate 441 underlying the planar inductor 440. Optionally, an insulator layer 444 may cover the top of the planar inductor 440.

FIG. 6G depicts a modification of the embodiment of FIGS. 6E-6F, in which half-circular ferrite cores 450a, 450b, 450c, etc., overlie respective sections of the planar inductor 440. The ferrite cores 450a, 450b, 450c, etc., confine the local magnetic fields producing the respective eddy current loops, hence producing a more confined eddy current and enhancing signal output.

FIGS. 6H and 6I depict an embodiment in which the individual ferrite cores 450a, 450b, 450c, etc., of FIG. 6D are replaced by an integrated ferrite core layer 450 providing continuous coverage of the planar inductor 440 along its entire length.

Figure 6J:
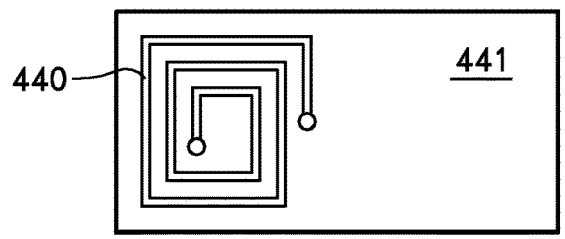

FIG. 6J depicts and embodiment in which the conductor of the planar inductor 440 is wound in a rectangular spiral.

Figure 7A:
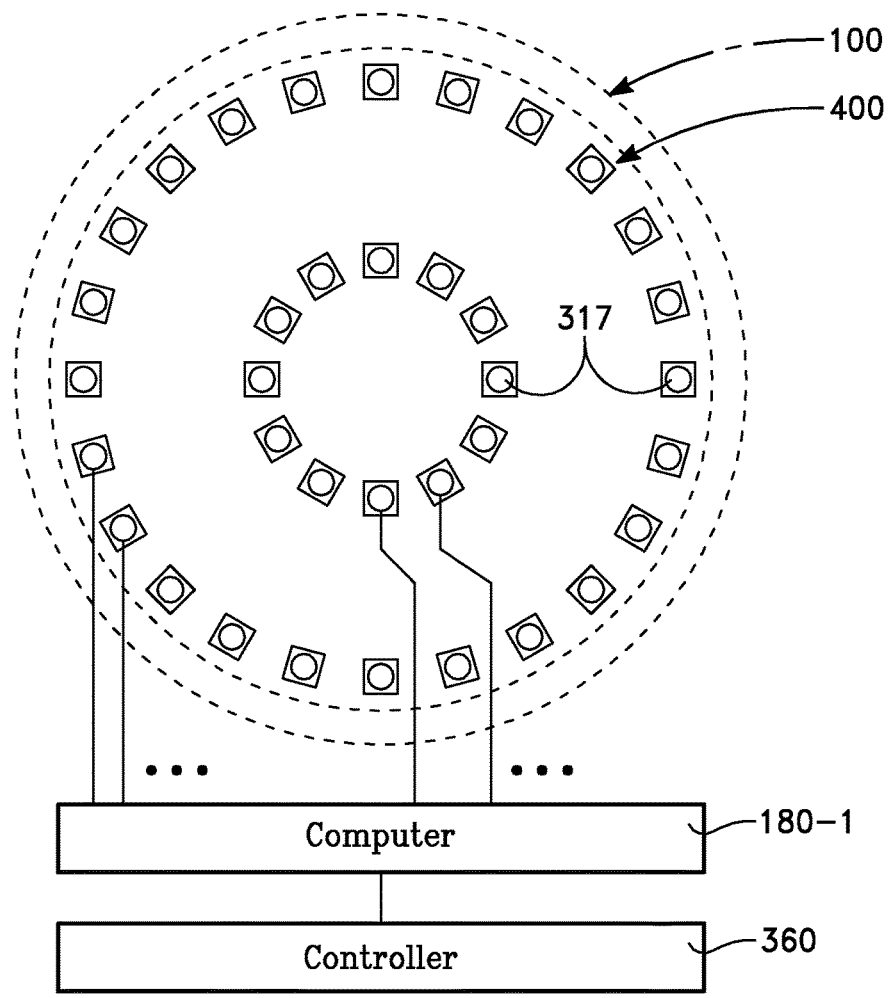
FIG. 7A includes a plan view of one embodiment corresponding to FIG. 6A.
Figure 7B:
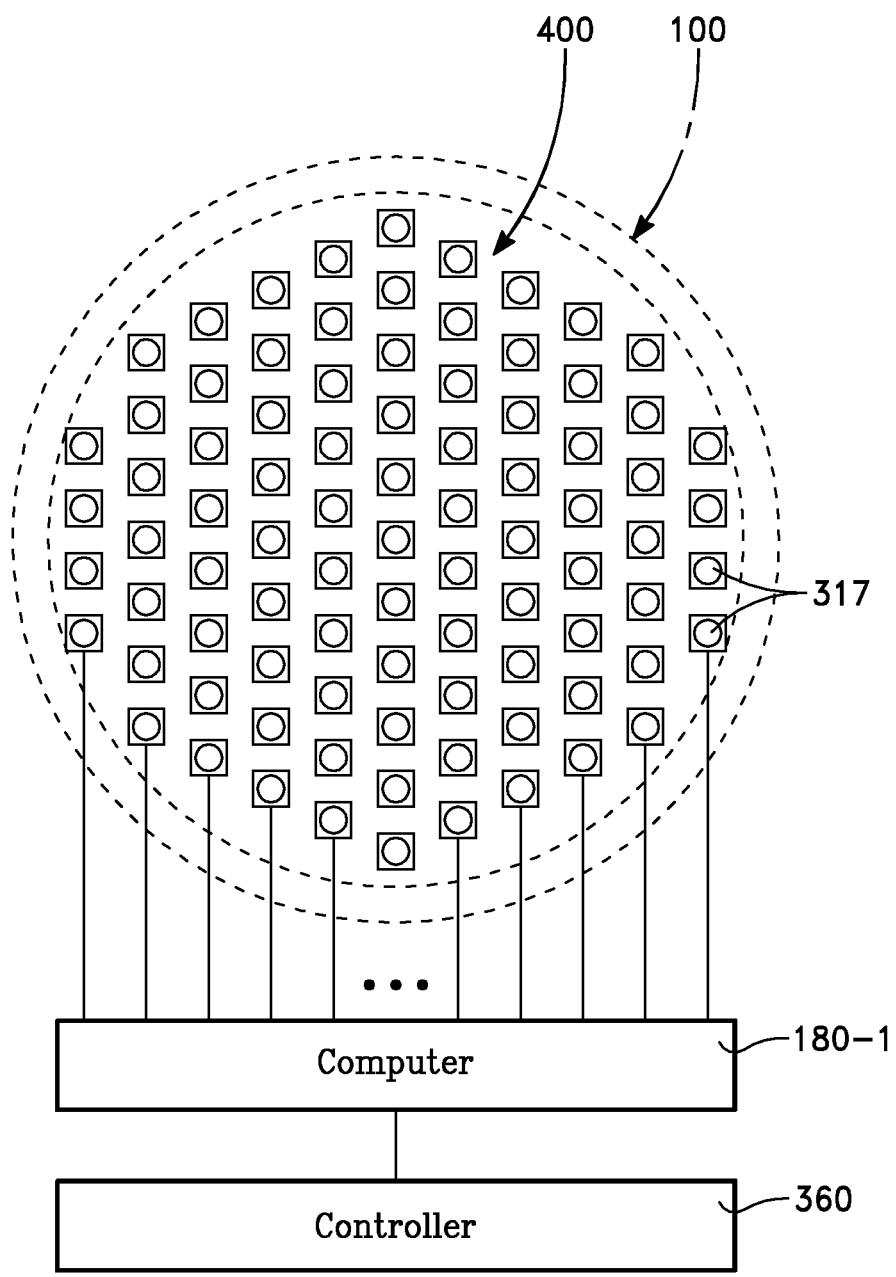
FIG. 7B includes a plan view of another embodiment corresponding to FIG. 6A.

Some embodiments may employ more than one eddy current sensor at each radial location. For example, plural eddy current sensors 400 may be disposed in circular arrays at different radial locations, as depicted in FIG. 7A. Further, the annular anodes may be replaced by circular arrays of discrete anodes 317, as depicted in FIG. 7A, whose voltages are individually controlled by the controller 360. In FIG. 7A, the discrete anodes 317 are submerged in the solution 305, while the array of eddy current sensors 400 are on the wafer back side and above the solution 305. In another embodiment depicted in FIG. 7B, the array of eddy current sensors 400 may be a two-dimensional array, and the anodes may be provided as a two dimensional array of discrete anodes 317 whose voltages are individually controlled by the controller 360. The computer 180-1 may be coupled to each individual sensor 400 in the array. This can enable the computer 180-1 to compensate for both radial non-uniformities and azimuthal non-uniformities in thickness distribution.

In one embodiment, the distribution model 181 of the barrier and seed layers determined for a given wafer by the energy beam measurement tool of FIG. 1A (or FIG. 3A) is used to determine an optimum initial distribution of anode voltages prior to the beginning of the electroplating process performed on the same wafer by the electroplating reactor of FIG. 6A. In one embodiment, the controller 360 (or the computer 180-1) of FIG. 6A receives a feed forward signal 362 from the beam measurement tool of FIG. 1A or 3A. The feed forward signal 362 is derived from the distribution model 181 (FIG. 1A or 3A), and represents the distribution or distribution non-uniformity of a chosen characteristic (e.g., sheet resistance or thickness) of the underlying barrier and seed layers. The controller 360 (or the computer 180-1) determines from the feed forward signal 362 a desired voltage ratio between the anode voltage sources 320, 325 to correct the non-uniformity. The controller 360 (or the computer 180-1) may be programmed to determine the optimum voltage ratio based upon non-uniformity in a measured distribution of sheet resistance, for example. After the electroplating process has begun, process control passes to the feedback control loop of FIG. 6A described above, which uses the thickness measurements taken in real time by the array of eddy current sensors 400.

In one version of the embodiment of FIG. 6A, each eddy current sensor 400 may be pressed against the back side of the wafer 100, providing a fixed displacement during plating between the eddy current sensor and the plating interface at the front (device) side of the wafer. (In such a case, the capacitance sensor 546 of FIG. 6E may be eliminated, to simplify the hardware.) This feature is advantageous because the eddy current signal is sensitive to the distance of the sensor from the wafer being measured. Keeping this displacement constant during plating facilitates precise sheet resistance and thickness measurements.

Sensors with different resolutions or sensitivities may be placed at optimal locations on the wafer. Early-stage plating at the wafer edge is particularly critical, for example, and a very sensitive eddy current sensor may be placed near the edge of the wafer. In the embodiment of FIG. 6A, the plural eddy current sensors 400 may be selected for different thickness ranges to provide a combination of optimal sensitivity and optimal range for different thicknesses of the metal layer 105. For example, in one embodiment, a first one of the eddy current sensors 400 may be selected to provide high sensitivity for the very thin Cu films that are encountered at the start of plating (e.g., less than 150 Angstroms thick). This high-sensitivity sensor saturates as the film gets thicker. A second one of the sensors 400 is selected with a lower resolution and larger range, to measure thicker films (e.g., 150-2000 Angstroms thick) with reduced absolute resolution, so as to complement the first (high-sensitivity) sensor.

Multiple eddy current sensors 400 with successive overlapping ranges may be provided in a further embodiment, as follows:

first sensor range: 0-150 Angstroms
second sensor range: 125-275 Angstroms
third sensor range: 250-750 Angstroms
fourth sensor range: 500-1500 Angstroms
fifth sensor range: 1200-2000 Angstroms.

The in situ closed loop feedback control described above with reference to FIG. 6A enables uniform plating thickness across the wafer. Well-controlled temporal and spatial plating rates are also critical to avoid formation of voids in a damascene structure as it is filled during plating. Variations or non-uniformities in thickness distribution can be corrected after the electroplating process during chemical mechanical polishing (CMP), but voids are unrecoverable sources of yield loss.

A sequence over time of successive thickness measurements by the array of eddy current sensors 400 may be used by the computer 180-1 to obtain a relative measure of change in sheet-resistance and thickness. From a time-series of measurements in the embodiment of FIG. 6A, the computer 180-1 can provide the user with an estimate of plating rates at different times and relative plating rates at different locations around the wafer without precise calibration of absolute sensor levels. The full time series of eddy current sensor outputs can also be fit to a straight line (or other suitable function) to provide a much more precise measure of rate of sheet resistance change than one or two discrete measurement points.

The measurement through the wafer back side in the embodiment of FIG. 6A can be carried out using sensors other than eddy current sensors. Acoustic sensors could, for example, be used to detect voiding in a particular area of the wafer.

Routing signals from the sensors 400 on the back side of the wafer to the computer 180-1 may be carried out while the wafer is rotated in the solution 305 by the wafer handling apparatus 410 above the wafer. Signals are passed through a rotating member of the wafer handling apparatus 410 in such a case. An alternative mode uses wireless signal transmission, which is possible in this environment in which most of the enclosure is plastic.

Rapid Acquisition of Thickness Distribution after Electroplating:

After completion of the electroplating process, a final measurement of metal thickness and spatial distribution of the thickness is needed. Such a final measurement facilitates, for example, monitoring the integrity of the contact ring 130 and of the peripheral contact belt 115. This latter measurement entails measuring metal thickness along the length of the peripheral contact belt 115 following completion of the electroplating process. Conventional use of an eddy current sensor to perform such measurements involves the taking of many discrete samples at successive locations at which the sensor is temporarily held stationary, which is time consuming and entails a significant expense.

Figure 8:
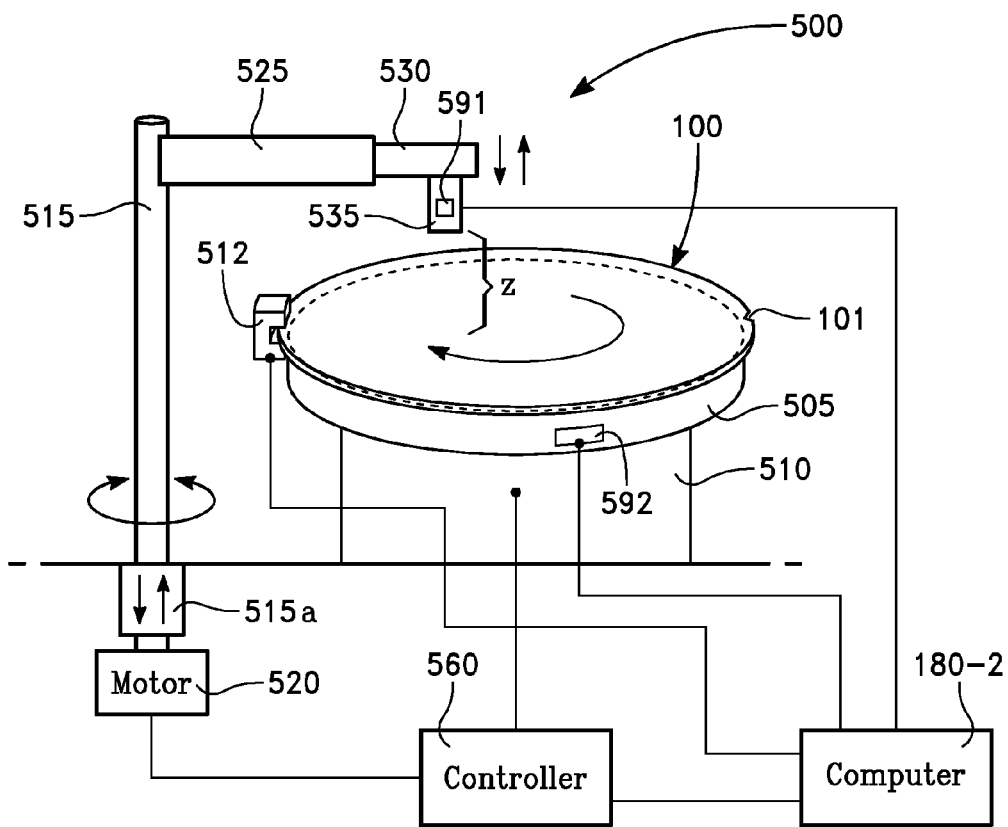
FIG. 8 includes a block diagram of a high speed thickness measurement tool in accordance with an embodiment.
Figure 9:
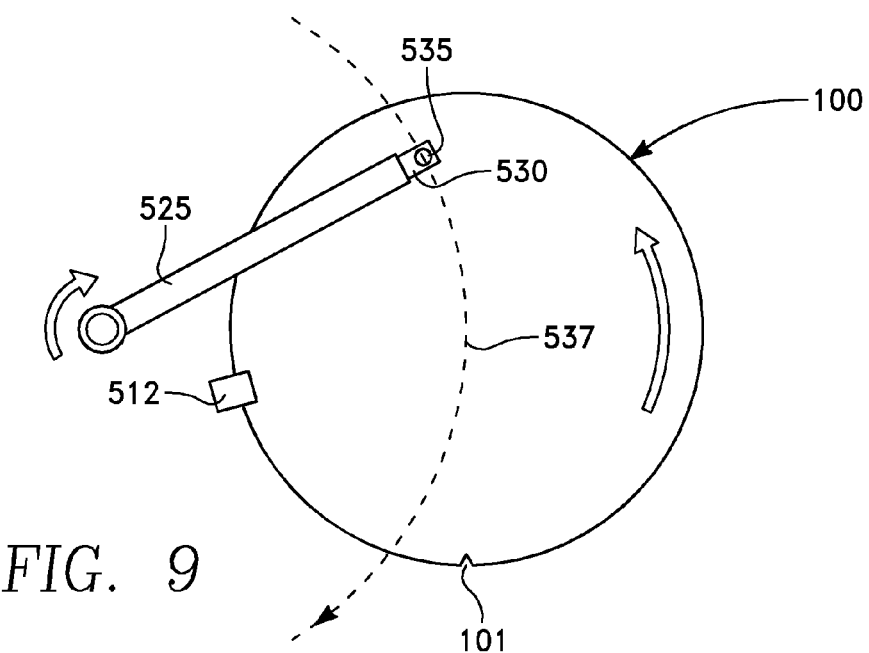
FIG. 9 is a plan view corresponding to FIG. 8.

This problem is solved in the embodiment of FIGS. 8 and 9, in which a continuous measurement of electroplated thickness distribution is performed by spinning the wafer at a high rate under an eddy current sensor suspended over the wafer front side, and changing the radial position of the eddy current sensor. In one embodiment, the eddy current sensor output is constantly sampled and correlated with successive radial and azimuthal positions of the eddy current sensor relative to the wafer, to rapidly acquire an accurate spatial image of thickness distribution.

Referring now to FIG. 8, a measurement tool 500 is capable of rapidly measuring thickness distribution across a wafer surface. The measurement tool 500 includes a vacuum chuck 505 for holding the wafer 100, a spinning stage 510 supporting the vacuum chuck 505 and a notch detector 512 stationed over or adjacent the wafer edge for detecting a notch 101 in the wafer edge (to measure the wafer rotational position). The measurement tool 500 further includes a rotatable vertical post 515, a rotation motor 520 coupled to the vertical post 515, a horizontal swing arm 525, a piezo electric vertical position actuator or transducer 530 and an eddy current sensor 535 mounted on the transducer 530. In a modification depicted in FIG. 8A, there is an array of plural eddy current sensors 535*a* through 535*f* mounted on the transducer 530, as will be described later herein.

Figure 10:
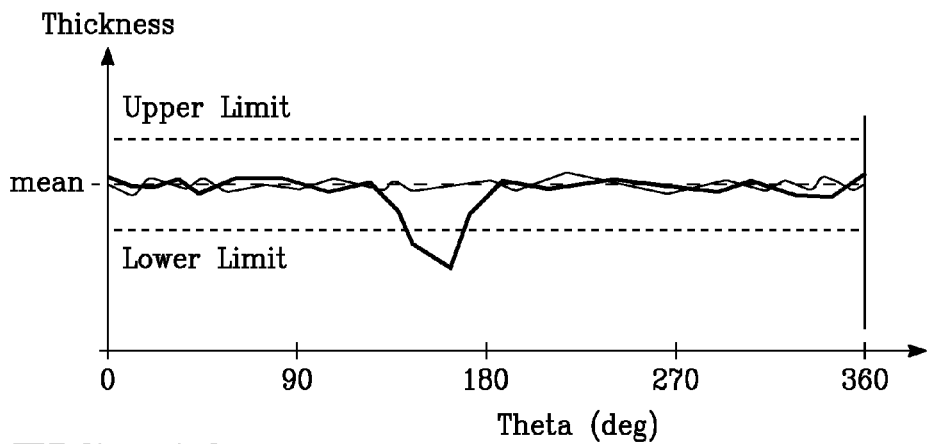
FIG. 10 is a graph representing measurement data obtained in the embodiment of FIG. 8.

In one embodiment, the vertical post 515 includes an actuator 515*a* to raise or lower the arm 525 and the eddy current sensor 535 together in a coarse vertical motion, whereas the transducer 530 enables a finer vertical motion for a better control of the lift-off distance Z between the eddy current sensor 535 and the wafer surface. As depicted in FIG. 9, the wafer 100 rotates with the spinning stage 510 while the eddy current sensor 535 is moved radially over the wafer 100 along an arcuate path 537. A continuous measurement signal from the eddy current sensor 535 is recorded (or successively sampled) by a computer 180-2 as a function of location on the wafer. This location is constantly shifted over time, in the manner depicted in FIG. 9. The computer 180-2 governs a controller 560 that controls the rotation motor 520 and the spinning stage 510. An output signal of the notch detector 512 is coupled to the computer 180-2. The location of the measurement is inferred by the computer 180-2 from the instantaneous angular position of the swing arm 525, the rotational speed of the spinning stage 510 and the elapsed time since the notch detector 512 last detected the notch 101. The recordation of such a continuous measurement is depicted in the graph of FIG. 10 for a fixed radial position of the eddy current sensor 535. The vertical axis of FIG. 10 represents measured thickness while the horizontal axis represents azimuthal (angular) position around the axis of the wafer. The allowable maximum and minimum thickness limits are superimposed in the graph, from which the computer 180-2 identifies out-of-tolerance conditions. Different graphs like that of FIG. 10 are produced for different radial positions of the eddy current sensor 535.

Figure 11:
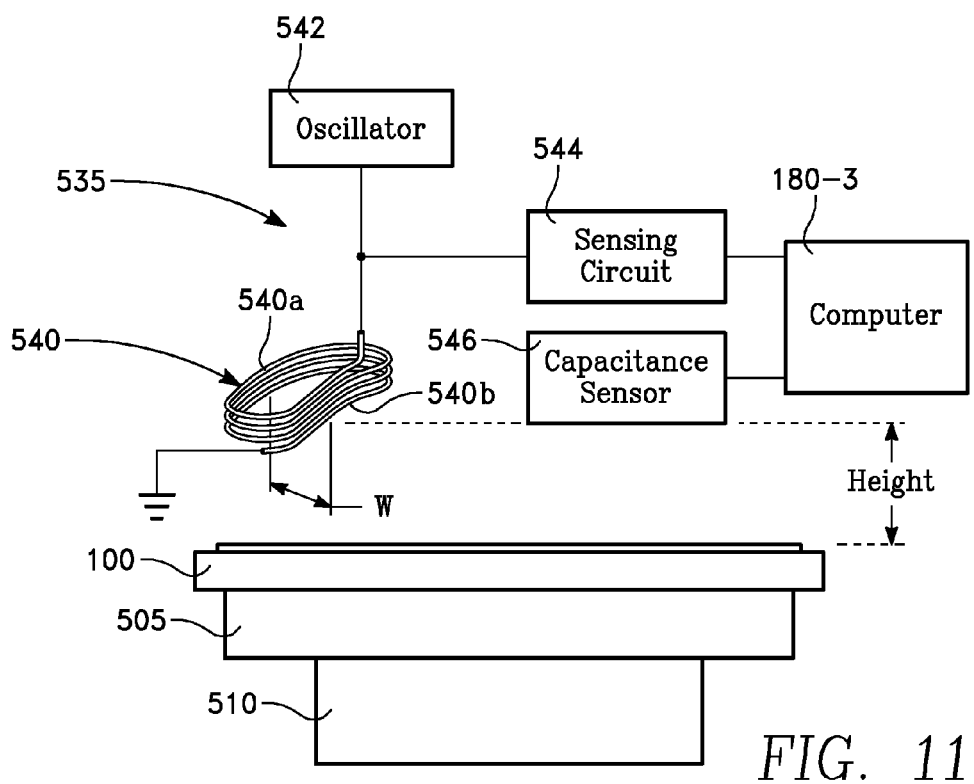
FIG. 11 illustrates an eddy current sensor adapted for use in the embodiments of FIGS. 8 and 8A and having a shaped measuring zone such as an arcuate shape.

FIG. 11 depicts an embodiment of the eddy current sensor 535 having a shaped measuring zone, for use in any of the embodiments of FIGS. 8-9 and 12-14. The eddy current sensor of FIG. 11 includes a coil 540, an RF oscillator 542 driving the coil 540, an impedance sensing circuit 544 coupled to the coil 540, and a computer 180-3 connected to the output of the impedance sensing circuit 544. Changes in underlying material thickness change the RF impedance of the coil 540, which are detected by the impedance sensing circuit 544, and correlated by the computer 180-3 to a thickness measurement. A displacement sensor or capacitance sensor 546 monitors the lift-off distance or height of the coil 540 above the wafer surface. In one embodiment, the measured lift-off distance is used by the computer 180-3 to calibrate each measurement accordingly. In one embodiment, the bottom of the capacitance sensor 546 may be co-planar with the bottom of the coil 540. In addition, or alternatively, the lift-off distance measured by the capacitance sensor 546 is used to construct a corrective feedback signal to the transducer 530 in a feedback loop to maintain a constant lift-off distance Z. In one embodiment, the corrective feedback signal is constructed by the computer 180-3 based upon the output of the capacitance sensor 546. The effect of the offset position between the eddy-current and capacitance sensors can be eliminated by synchronizing the motion and the data acquisition. The shape of the eddy current field, determined by the shape or footprint of the coil 540, can also be optimized for a particular geometry. A long thin or even a curved sensor can be employed to provide an average reading for a particular region of the wafer such as the periphery or circumference of the wafer. For example, FIG. 11 depicts the coil 540 having an arcuate geometry, and has an arcuate footprint or measuring zone defined by the shape of the coil 540. In the illustrated embodiment, the boundary of the coil 540 in its bottom plane includes a pair of generally congruent or parallel arcs 540*a*, 540*b* displaced from one another by a distance W corresponding to the width of the sensor footprint. In one embodiment, the parallel arcs 540*a*, 540*b* may each have a radius centered at the axis of symmetry of the wafer 100. While the coil 540 in the illustrated embodiment of FIG. 11 is helically wound, in another embodiment the coil 540 may be replaced by the planar inductor 440 of FIGS. 6B-6I described above.

While this specification refers to several computers 180, 180-1, 180-2 and 180-3, it is understood some or all of the computers referred to may be implemented as a single computer.

FIG. 12 depicts a modification of the embodiment of FIG. 9 employing a gantry 570 to control movement of the eddy current sensor 535 along one axis. FIG. 13 depicts a modification of the embodiment of FIG. 9 in which the swing arm 525 is retractable to adjust the radial position of the eddy current sensor 535. FIG. 14 depicts a modification of the embodiment of FIG. 9, in which the spinning stage 510 provides translational movement of the wafer 100 along either (or both) X- and Y-axes or along a radial direction and vertical motion to adjust lift-off distance Z, in addition to spinning the wafer 100, while the eddy current sensor 535 is stationary on a fixed mount 536.

The method performed by the apparatus of any of FIGS. 8-14 has the advantage of providing a more complete picture of the thickness variation along a particular radius. It is well-suited to detect thickness excursions along the edge of the wafer. Small spatial non-uniformities are not missed because all positions along the edge are continuously measured. It is also a fast measurement. The wafer can be rotated at more than 1 revolution per second. For example, in 1 second, several snapshots of the thickness profile at a certain radius are collected. The multiple snapshots can be averaged to reduce noise, and to amplify small thickness non-uniformity. Discrete-point information can be extracted by synchronizing the motion and the data acquisition with the aid of the notch detector to orient the wafer.

Figure 8A:
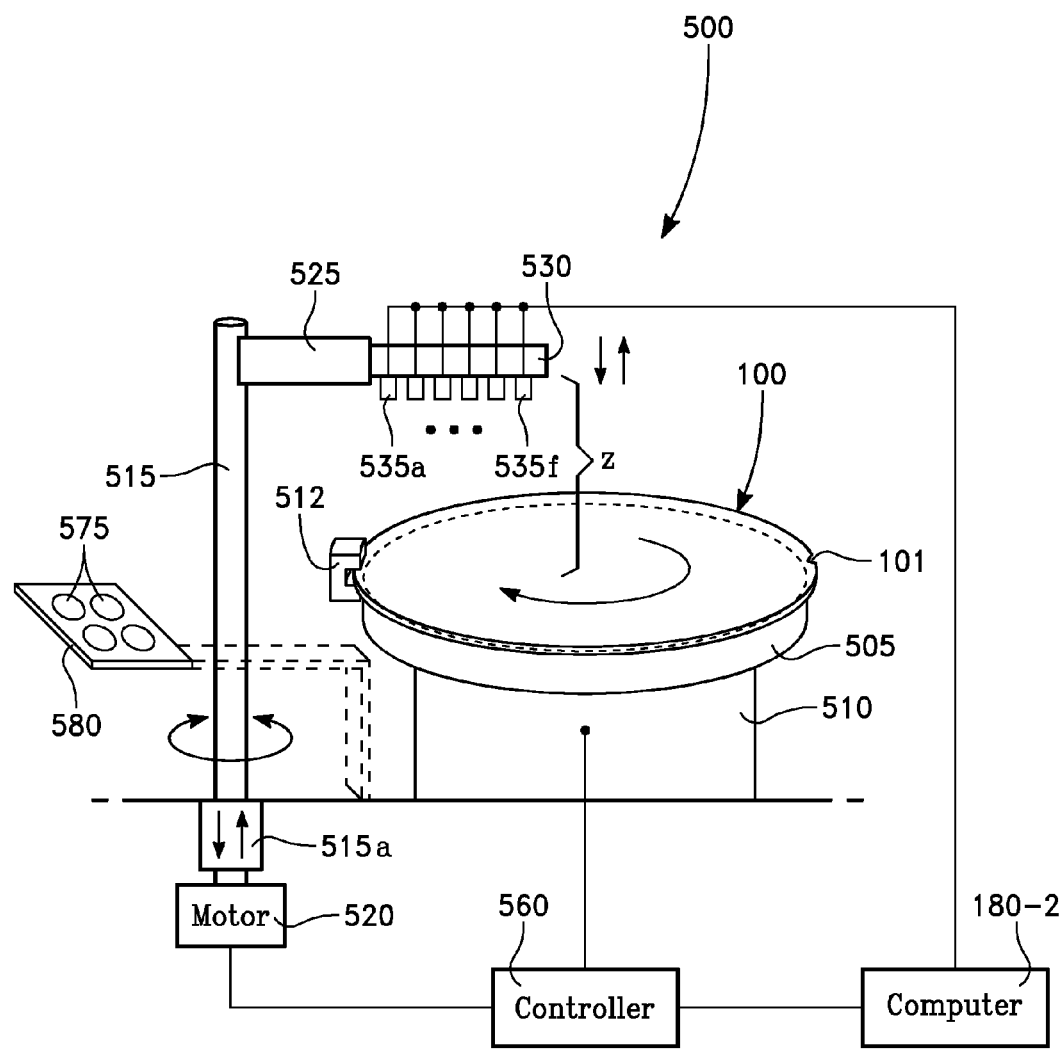
FIG. 8A includes a block diagram of a high speed thickness measurement tool in accordance with a further embodiment.

Faster data acquisition can be performed by attaching multiple (e.g. N) eddy current sensors, such as the sensors 535*a*-535*f* of FIG. 8A, on the transducer 530. The sensors 535*a*-535*f* may be arranged along an imaginary straight line extending radially with respect to the axis of the vertical post 515. Alternatively, the sensors 535a-535f may be mounted in this manner on the transducer 530 in the embodiments of FIGS. 12 and 13 or on the fixed mount 536 of FIG. 14. The sensors 535a-535f may form or be included in an array of N sensors where N is an integer. The N sensors including the sensors 535a-535f sweep multiple radii simultaneously in a single wafer rotation, collecting N times as much data as a single sensor would collect. Signal matching from the N sensors can be provided by careful calibration of each sensor using a common set of reference films 575 with known thickness. In one embodiment, the set of reference films 575 may be mounted on a tray 580 located near the side or perimeter of the vacuum chuck 505, outside the diameter (e.g., 300 mm) of the wafer 100 (as depicted in FIG. 8A). Periodic re-calibration of the sensors 535a-535f is conducted as needed.

Improvements in the thermal stability of the measurement apparatus of FIG. 8 can be achieved by including a temperature sensor 591 (e.g., a thermocouple, or resistance temperature detector) inside the eddy current sensor 535, and including a temperature sensor 592 in the vacuum chuck 505 to measure the wafer temperature. The information from the temperature sensors 591 and 592 can be used by the computer 180-2 to compensate for any thermal drift in the coil and the wafer that can affect the eddy-current signal. The signal compensation is possible when the signal is pre-calibrated vs. temperature during the initial set-up.

For measurements involving a blanket conductive film deposited on top of another conductive film or patterned conductive structures, the underlying layer/pattern can induce appreciable eddy-current signal that may interfere with the signal of interest from the top-most layer. In such a situation, two measurements can be taken: the first one is before the deposition of the layer of interest, the second one is after the deposition. The first measurement will map the signal variation from the underlying layer/pattern throughout the wafer, which can then be subtracted from the second measurement, such that the true thickness variation of the top layer of interest can be accurately measured.

The high speed thickness measurement tool of FIGS. 8 and 9 may provide feedback correction to the electroplating reactor of FIG. 5A or 6A. Specifically, the computer 180-2 of FIG. 8 or FIG. 8A may be programmed to determine non-uniformity in the thickness distribution after the electroplating process is completed, and to generate a feedback correction signal 363 indicated in FIG. 6A. In the electroplating reactor of FIG. 5A or 6A, the controller 360 may be programmed to adjust the distribution of anode voltages to compensate for the non-uniformity in thickness distribution. The computer 180-2 may provide this correction signal either to the controller 360, as indicated in FIG. 6A, or to the electroplating reactor computer 180-1, for example.

Figure 15:
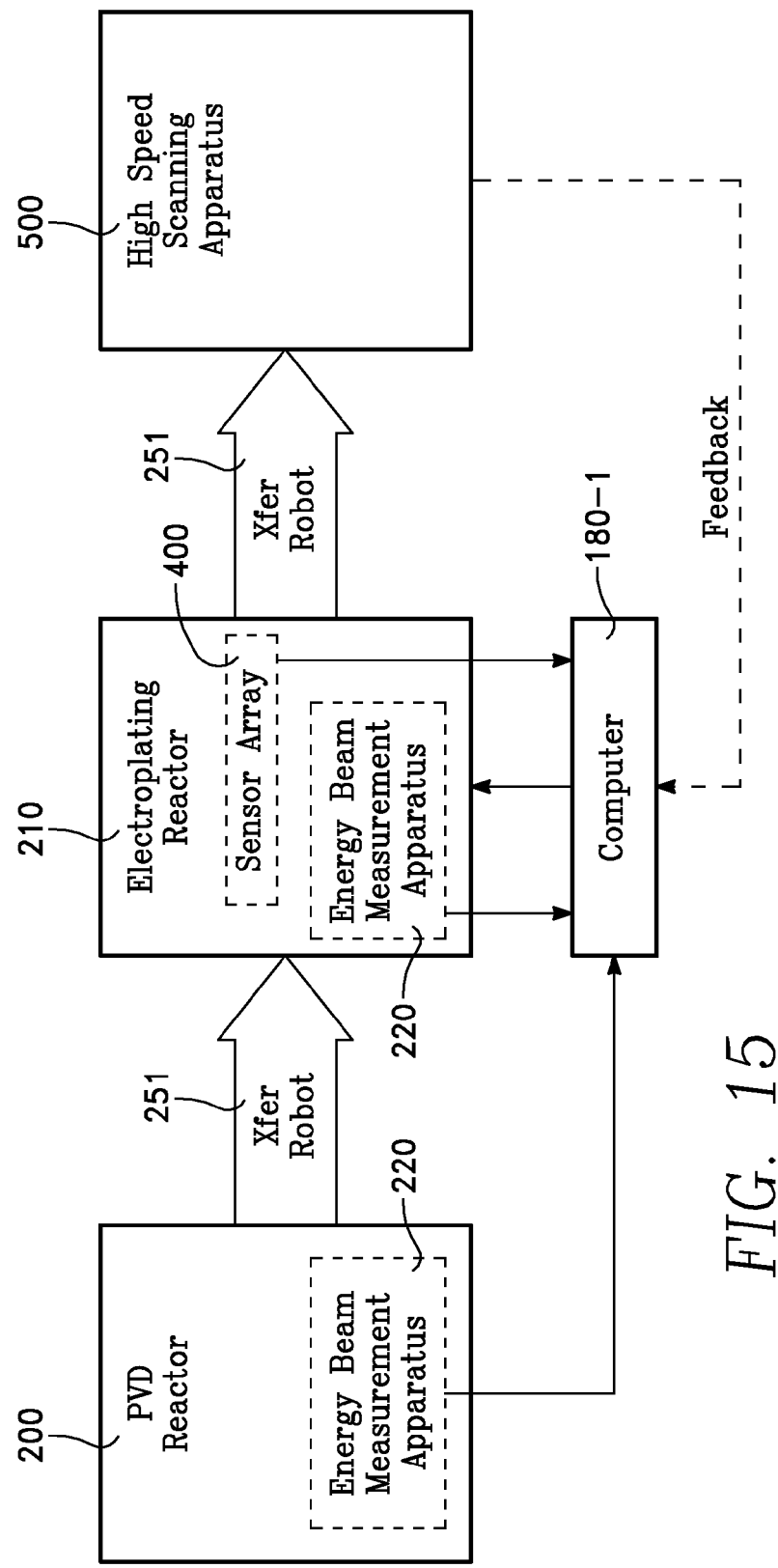
FIG. 15 is a schematic block diagram of an integrated system including the embodiments of FIGS. 1A, 6 and 8.

Integrated System with Feed Forward and Feedback Control:

FIG. 15 depicts an integrated system capable of performing feed forward control and feedback control of the electroplating process. The system includes the PVD reactor 200 of FIG. 4, an energy beam measurement tool 220 of the type described with respect to FIG. 1A or 3A, an electroplating reactor 210 of the type described above with reference to FIG. 6A having in situ feedback, and a measurement tool 500 of the type described above with reference to FIGS. 8-14. As depicted in FIG. 15, the energy beam measurement tool 220 may be in either one of two locations (e.g., in the PVD reactor 200 or in the electroplating reactor 210). In one embodiment, a wafer transfer robot 251 provides wafer transfer from the PVD reactor 200 to the electroplating reactor 210, and from the electroplating reactor 210 to the measurement tool 500. FIG. 16 depicts a process performed by the system of FIG. 15 employing feed forward control and feedback control.

The energy beam measurement tool 220 provides information to the electroplating reactor 210 defining non-uniformities in an incoming wafer prior to the beginning of the electroplating process. This information serves as feed forward control information, which the electroplating reactor 210 uses to establish an initial distribution of anode supply voltages to the array of electroplating anodes (e.g., the anode rings 310, 315 of FIG. 6A). The electroplating reactor 210 of FIG. 15 includes an array of eddy current sensors 400 providing real-time feedback of thickness distribution information used to control the distribution of anode supply voltages. The measurement tool 500 may be provided as a part of the electroplating reactor 210 (or separately), and measures a metal thickness distribution on a wafer upon completion of the electroplating process. The thickness distribution measurements by the measurement tool 500 for one wafer may (in one embodiment) be provided as feedback information for the next wafer to the electroplating reactor 210. The computer 180-1 may use this feedback information as a one-time correction to refine the anode supply voltage distribution of the electroplating reactor 210.

FIG. 16 illustrates one embodiment of a method in the system of FIG. 15. FIGS. 17A-17D depict changes in thin film structure corresponding to certain steps of FIG. 16. Referring now to FIG. 16, an initial step, depicted in FIG. 17A, is to form a trench 700 in a semiconductor layer or substrate 705 (block 600 of FIG. 16). The wafer is then transferred to the PVD reactor 200, in which a barrier layer 710 is deposited (block 610 of FIG. 16) as depicted in FIG. 17B. Optionally, the energy beam measurement tool 220 may be used to perform an initial measurement of sheet resistance distribution in the barrier layer 710 (block 615 of FIG. 16). Thereafter, a copper seed layer 715 is deposited over the barrier layer (block 620 of FIG. 16) as depicted in FIG. 17C. At this point, a final energy beam measurement of sheet resistance distribution is performed on the wafer (block 630 of FIG. 16), and this distribution is provided to the electroplating reactor 210 as feed forward control (block 640 of FIG. 16).

At or prior to the beginning of the electroplating process, the anode voltage distribution within the electroplating reactor 210 is initialized or set in accordance with feed forward information from the energy beam measurement tool 220. If this information indicates a particular non-uniformity in sheet resistance distribution, then the anode voltage distribution is initially configured to best compensate the non-uniformity. For example, a center-high sheet resistance distribution is a predictor of a center-high electroplating growth rate distribution. Therefore, such a non-uniformity may be compensated by a center-low anode voltage distribution in the electroplating reactor 210. Likewise, a center-low sheet resistance distribution measurement by the energy beam measurement tool 220 is compensated by a center-high anode voltage distribution in the electroplating reactor 210. The feed forward function of block 640 may be implemented by the computer 180-1 to achieve the above-described compensation, and the computer 180-1 may be programmed accordingly.

During the electroplating process (block 650 of FIG. 16), a thick copper layer 730 is deposited over the copper seed layer 715 and fills the trench 700, as depicted in FIG. 17D. The anode voltage distribution in the electroplating reactor 210 is adjusted in accordance with real-time feedback from the array of eddy current sensors 400 on the wafer back side (block 660 of FIG. 16). Such real time feedback indicates either a center-high or a center-low thickness distribution at each instant (sample) in time, which is compensated by a center-low or a center-high anode voltage distribution. The computer 180-1 may be programmed to provide such compensation in response to the feedback from the eddy current sensor array.

After completion of the electroplating process of a given wafer, the measurement tool 500 measures the thickness distribution across the wafer (block 670 of FIG. 16). This distribution, in one embodiment, is fed back to the electroplating reactor 210 as feedback to refine the anode voltage distribution for the next wafer. Thus, for example, a center-high thickness distribution measurement by the measurement tool 500 is compensated by adjusting the anode voltage distribution in the electroplating reactor 210 to be more center-low. Likewise, a center-low thickness distribution measurement by the measurement tool 500 is compensated by adjusting the anode voltage distribution in the electroplating reactor 210 to be more center-high. Such compensation may be controlled by the computer 181-1, which may be programmed accordingly.

While the foregoing is directed to embodiments of the present invention, other and further embodiments of the invention may be devised without departing from the basic scope thereof, and the scope thereof is determined by the claims that follow.

What is claimed is:

1. A measurement tool comprising:
   a workpiece support to support a workpiece;
   a contact ring facing said workpiece support and comprising plural axial contact rods arranged in a circle overlying and contacting a peripheral contact belt of said workpiece;
   a sensor and plural individually controllable switches connected between individual ones of said plural contact rods and said sensor;
   a beam source having an energy beam propagation direction toward a front side of said workpiece corresponding to a beam impact location on said front side;
   a translation mechanism capable of translating said beam source relative to said workpiece support; and
   a computer coupled to receive an output of said sensor, said computer being connected to said plural individually controllable switches, to said beam source and to said translation mechanism, said computer programmed to infer from the output of said sensor a material characteristic of a film on the front side of said workpiece.

2. The measurement tool of claim 1 wherein said peripheral contact belt of said workpiece is devoid of circuit elements.

3. The measurement tool of claim 1 wherein said switches are electrically isolated from one another.

4. The measurement tool of claim 1 wherein said computer is connected to control said switches.

5. The measurement tool of claim 4 wherein said computer is programmed to enable different ones of said switches in successive times, and to select different beam impact locations for different ones of said times by controlling said translation mechanism.

6. The measurement tool of claim 1 wherein said beam source produces a pulsed beam and wherein said computer is programmed to: (A) sense an RC decay time of an output of said sensor during an off-time of said pulsed beam, and (B) infer from said RC decay time a sheet resistance.

7. The measurement tool of claim 1 wherein said beam source produces a continuous beam, and wherein said computer is programmed to sense a magnitude of an output of said sensor.

8. The measurement tool of claim 1 wherein said beam source comprises a light source, said measurement tool further comprising an anode electrode facing said workpiece support and a voltage supply connected to said anode electrode.

9. The measurement tool of claim 1 further comprising a vacuum enclosure containing said workpiece support.

10. The measurement tool of claim 1 wherein said beam source comprises an electron beam source.

* * * * *